United States Patent
Hameed et al.

(10) Patent No.: US 11,119,053 B2
(45) Date of Patent: Sep. 14, 2021

(54) WIRELESS SENSING DEVICES INCLUDING STABLE NEAR-FIELD ANTENNA

(71) Applicant: 3M INNOVATIVE PROPERTIES COMPANY, St. Paul, MN (US)

(72) Inventors: Zohaib Hameed, Woodbury, MN (US); Nicholas T. Gabriel, Grand Rapids, MN (US); Ronald D. Jesme, Plymouth, MN (US); Christian Weinmann, Alsdorf (DE); Kristin J. Godbey, Vadnais Heights, MN (US); Bret W. Ludwig, Oakdale, MN (US); John P. Baetzold, North St. Paul, MN (US)

(73) Assignee: 3M INNOVATIVE PROPERTIES COMPANY, St. Paul, MN (US)

( * ) Notice: Subject to any disclaimer, the term of this patent is extended or adjusted under 35 U.S.C. 154(b) by 35 days.

(21) Appl. No.: 16/623,883

(22) PCT Filed: Jun. 13, 2018

(86) PCT No.: PCT/IB2018/054313
§ 371 (c)(1),
(2) Date: Dec. 18, 2019

(87) PCT Pub. No.: WO2018/234940
PCT Pub. Date: Dec. 27, 2018

(65) Prior Publication Data
US 2021/0148836 A1 May 20, 2021

Related U.S. Application Data

(60) Provisional application No. 62/524,124, filed on Jun. 23, 2017.

(51) Int. Cl.
*G01N 22/04* (2006.01)
*H01Q 1/22* (2006.01)
*H04B 5/00* (2006.01)

(52) U.S. Cl.
CPC ............. *G01N 22/04* (2013.01); *H01Q 1/225* (2013.01); *H01Q 1/2283* (2013.01); *H04B 5/0043* (2013.01)

(58) Field of Classification Search
CPC .... G01N 22/04; H04B 5/0043; H01Q 1/2283; H01Q 1/225
(Continued)

(56) References Cited

U.S. PATENT DOCUMENTS

2006/0148137 A1* 7/2006 Hartzell ................ B81C 1/0023
438/149
2007/0285324 A1 12/2007 Waterhouse
(Continued)

FOREIGN PATENT DOCUMENTS

JP 2006201068 A2 8/2006
JP 2016170071 A2 9/2016
(Continued)

OTHER PUBLICATIONS

International Search Report for PCT International Application No. PCT/IB2018/054313, dated Oct. 10, 2018, 3 pages.

*Primary Examiner* — Lam T Mai
(74) *Attorney, Agent, or Firm* — Yufeng Dong

(57) ABSTRACT

Wireless sensing devices including stable near-field antennas are provided. A spacer layer is attached to a portion of the substrate adjacent to the antenna. The spacer layer has a thickness T, a relative permittivity k, and a figure of merit defined as the ratio of T (in micrometers) by k. The spacer layer has the figure of merit no less than 20 (micrometers).

20 Claims, 16 Drawing Sheets

(58) Field of Classification Search
USPC .......................................................... 343/703
See application file for complete search history.

(56) References Cited

U.S. PATENT DOCUMENTS

| | | | |
|---|---|---|---|
| 2010/0099367 A1* | 4/2010 | Shamim ................... | G01T 1/026 |
| | | | 455/95 |
| 2011/0018689 A1* | 1/2011 | McAllister ....... | G06K 19/07758 |
| | | | 340/10.1 |
| 2014/0065397 A1 | 3/2014 | Johnson | |
| 2016/0006476 A1* | 1/2016 | El-Rayis .................. | H04B 1/18 |
| | | | 455/78 |
| 2016/0149292 A1 | 5/2016 | Ganton | |
| 2016/0338639 A1 | 11/2016 | Myers | |
| 2016/0340227 A1* | 11/2016 | Renz ........................ | C03B 32/00 |
| 2016/0340228 A1* | 11/2016 | Schreder ............... | C03B 17/067 |
| 2016/0340229 A1* | 11/2016 | Niessner ............... | C03B 11/125 |
| 2017/0079583 A1 | 3/2017 | Cardinali | |
| 2017/0357886 A1* | 12/2017 | Kawamura ........ | G06K 19/0716 |
| 2018/0263827 A1 | 9/2018 | Omori et al. | |
| 2020/0400466 A1* | 12/2020 | Iannotti ................ | H01Q 1/2225 |

FOREIGN PATENT DOCUMENTS

| | | |
|---|---|---|
| WO | WO 2001-089034 | 11/2001 |
| WO | WO 2013-147799 | 10/2013 |
| WO | WO 2013-191178 | 12/2013 |
| WO | WO 2016-018585 | 2/2016 |
| WO | WO 2016-018777 | 2/2016 |
| WO | WO 2016-073344 | 5/2016 |
| WO | WO 2016-160359 | 10/2016 |
| WO | WO 2017094794 | 6/2017 |
| WO | WO 2017-218619 | 12/2017 |

* cited by examiner

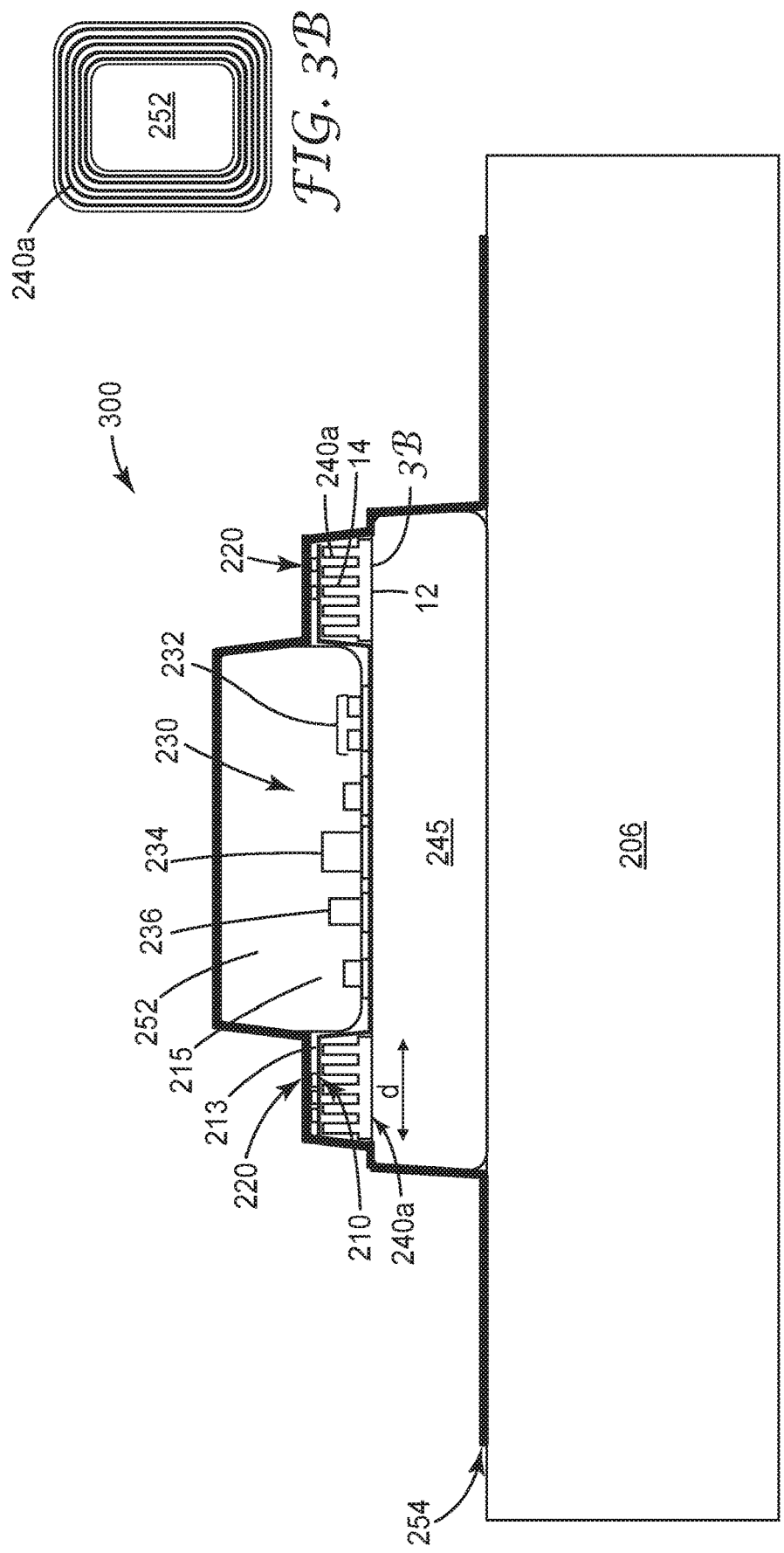

WIRELESS SENSING DEVICES INCLUDING STABLE NEAR-FIELD ANTENNA

CROSS REFERENCE TO RELATED APPLICATIONS

This application is a national stage filing under 35 U.S.C. 371 of PCT/IB2018/054313, filed Jun. 13, 2018, which claims the benefit of U.S. Application No. 62/524,124, filed Jun. 23, 2017, the disclosure of which is incorporated by reference in its/their entirety herein.

TECHNICAL FIELD

The present disclosure relates to wireless sensing devices including a stable near-field antenna, and methods of making and using the sensing devices.

BACKGROUND

Portable electronic devices have been widely used. There has been a trend towards "connected" culture where a person carries or wears a range of devices and sensors constantly communicating with each other and the outside world. A key to achieving this is flexible, wearable electronics including near-field antennas.

SUMMARY

There is a desire to provide near-field antennas having predictable performance (e.g., a stable resonant frequency and/or quality factor) to electronic devices, for example, when the devices are present in an environment with a moisture variation (e.g., on a human skin or fluid collection media). The present disclosure describes wireless sensing devices including a stable near-field antenna, and methods of making and using the sensing devices.

In one aspect, the present disclosure describes a radio-frequency (RF) sensor device including a substrate, an antenna having at least a portion disposed on a first portion of the substrate, a sensor disposed on a second portion of the substrate, the sensor being at least partially surrounded by the antenna, the sensor including an RF component electrically coupled to the antenna, and a spacer layer attached to the first portion of the substrate adjacent to the antenna. The spacer layer has a thickness T, a relative permittivity k, and a figure of merit defined as the ratio of T (in micrometers) by k, the spacer layer has the figure of merit no less than 20 (micrometers). The relative permittivity or dielectric constant k in the present disclosure refers to the relative permittivity of the material of a spacer layer that is expressed as a ratio of its absolute permittivity to the permittivity of vacuum. The values of the relative permittivity k are to be measured according to ASTM standard D150 at room temperature under the frequency range of, for example, about 10 KHz to about 10 MHz.

In another aspect, the present disclosure describes a radio-frequency (RF) sensor device including a substrate, an antenna having at least a portion disposed on a peripheral portion of the substrate, a sensor disposed on a central portion of the substrate, and a spacer layer attached to the peripheral portion of the substrate adjacent to the antenna. The spacer layer has a thickness T, a relative permittivity k, and a figure of merit defined as the ratio of T (in micrometers) by k, the spacer layer has the figure of merit no less than 20 (micrometers). The sensor may include an RF component electrically coupled to the antenna.

In another aspect, the present disclosure describes an RF sensor to measure a hydration level. The sensor includes a substrate, an antenna having at least a portion disposed on a peripheral portion of the substrate, an absorption element including a fluid absorption material, and a spacer layer attached to the peripheral portion of the substrate adjacent to the antenna. The spacer layer has a thickness T, a relative permittivity k, and a figure of merit defined as the ratio of T by k, the spacer layer has the figure of merit no less than 20 (micrometers). A sensor element is disposed on the substrate. The sensor element is positioned proximate to the absorption element and configured to measure the hydration level of the absorption element. The sensor element is at least partially surrounded by the antenna and electrically coupled to the antenna.

Various unexpected results and advantages are obtained in exemplary embodiments of the disclosure. One such advantage of exemplary embodiments of the present disclosure is that a spacer layer provided for an antenna of wireless sensing devices can prevent unpredictable performance of the antenna in the presence of an adjacent volume of material having a variable moisture. In some embodiments, the wireless sensing devices include a hydration sensor to measure a hydration level of the adjacent volume of material (e.g., a skin, an absorption element or fluid collection media, etc.).

Various aspects and advantages of exemplary embodiments of the disclosure have been summarized. The above Summary is not intended to describe each illustrated embodiment or every implementation of the present certain exemplary embodiments of the present disclosure. The Drawings and the Detailed Description that follow more particularly exemplify certain preferred embodiments using the principles disclosed herein.

BRIEF DESCRIPTION OF THE DRAWINGS

The disclosure may be more completely understood in consideration of the following detailed description of various embodiments of the disclosure in connection with the accompanying figures, in which:

FIG. 3A illustrates a cross-sectional view of a wireless sensing device, according to another embodiment.

FIG. 3B illustrates a top view of the wireless sensing device of FIG. 3A.

Figure 1A:
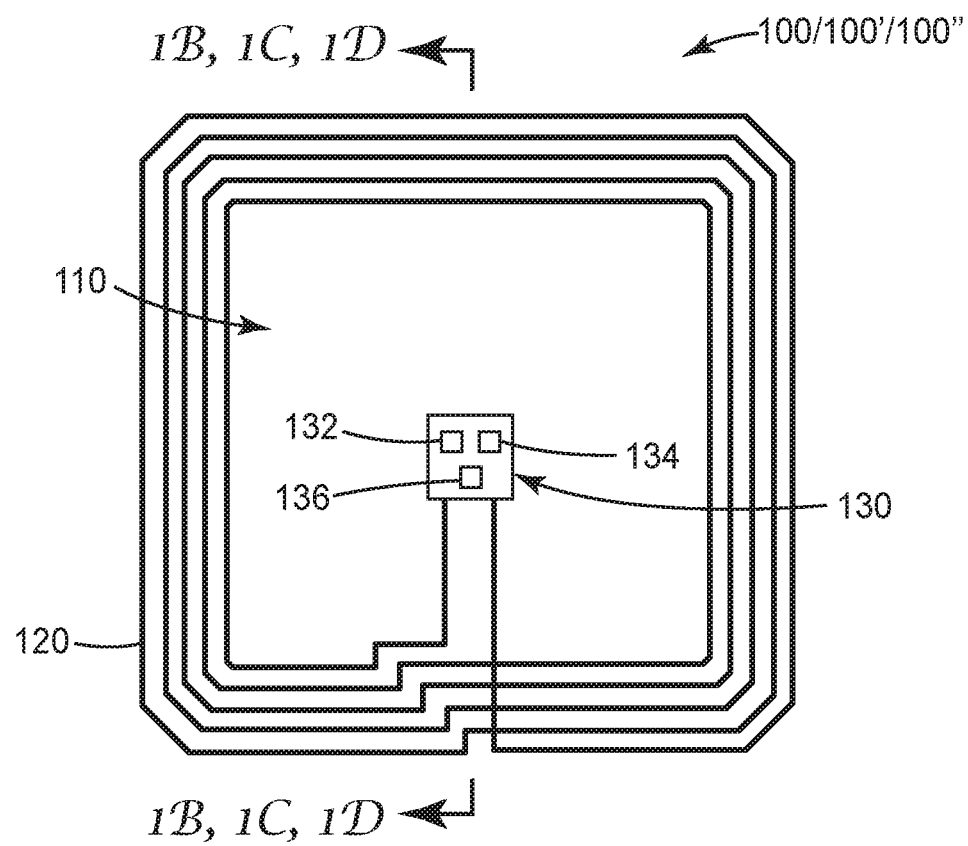
FIG. 1A illustrates a schematic top view of a wireless sensing device including an antenna, according to one embodiment.
Figure 1B:
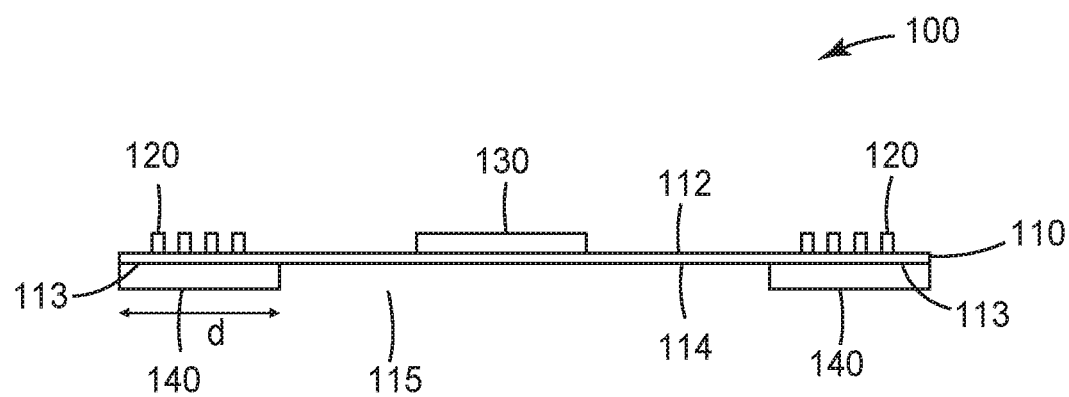
FIG. 1B illustrates a cross-sectional view of the wireless sensing device of FIG. 1A, according to one embodiment.

In the drawings, like reference numerals indicate like elements. While the above-identified drawing, which may not be drawn to scale, sets forth various embodiments of the present disclosure, other embodiments are also contemplated, as noted in the Detailed Description. In all cases, this disclosure describes the presently disclosed disclosure by way of representation of exemplary embodiments and not by express limitations. It should be understood that numerous other modifications and embodiments can be devised by those skilled in the art, which fall within the scope and spirit of this disclosure.

DETAILED DESCRIPTION

The present disclosure provides wireless sensing devices including a stable near-field antenna, and methods of making and using the sensing devices. A spacer layer having relatively low dielectric constant is provided for an antenna of the wireless sensing devices to prevent unpredictable performance of the antenna in the presence of an adjacent volume of material having a variable moisture. In some embodiments, the wireless sensing devices include a hydration sensor to measure a hydration level of the adjacent volume of material (e.g., fluid collection media). In some embodiments, the present disclosure provides a radio-frequency (RF) sensor device including a substrate, an antenna having at least a portion disposed on a first portion of the substrate, a sensor disposed on a second portion of the substrate, and a spacer layer attached to the first portion of the substrate adjacent to the antenna.

FIGS. 1A-D illustrate wireless sensing devices 100, 100' and 100", according to some embodiments. The wireless sensing device 100, 100' or 100", or referred to as a radio-frequency (RF) sensor tag, includes a substrate 110, an antenna 120, a sensing circuit 130 electronically coupled to the antenna 120, and one or more spacer layers 140 and/or 140'. The substrate 110 has a first major surface 112 and a second major surface 114 opposite to the first major surface 112. The antenna 120 is disposed on a peripheral portion 113 or 113' of the major surface 114 or 112 of the substrate 110. The sensing circuit 130 is disposed on the first major surface 112 and at least partially surrounded by the antenna 120. The sensing circuit 130 includes an RF component 132 electrically coupled to the antenna 120. Exemplary sensing circuits are described in WO 2016/073344 (Jesme et al.), which is incorporated herein by reference.

The substrate 110 can be flexible or rigid. In some embodiments, the substrate 110 can be stretchable. In some embodiments, the substrate 110 can include a polymeric film. In some embodiments, the substrate 110 may include polyurethane. Suitable polymer films may include, for example, elastomeric polyurethane, co-polyester, polyether block amide films, etc. It is to be understood that the substrate 110 can made of any suitable materials for flex circuits.

The spacer layer 140 and/or 140' can be attached to the peripheral portion of the substrate 110 adjacent to the antenna 120. In the depicted embodiment of FIG. 1B, the spacer layer 140 is disposed on the peripheral portion 113 of the second major surface 114 of the substrate 110, opposite to the antenna 120. In the depicted embodiment of FIG. 1C, the spacer layer 140' is disposed on the peripheral portion 113' of the first major surface 112 to cover the antenna 120. In the depicted embodiment of FIG. 1D, the spacer layer 140 is disposed on the peripheral portion 113 of the second major surface 114 of the substrate 110, opposite to the antenna 120; and the spacer layer 140' is disposed on the peripheral portion 113' of the first major surface 112 to cover the antenna 120.

It is to be understood that the spacer layers 140, 140' can be positioned at any suitable locations adjacent to the antenna 120 to prevent unpredictable performance of the antenna in the presence of an adjacent volume of material having a variable moisture. The antenna along with the spacer layer can have at least a portion disposed on a first portion of the substrate, while the sensing circuit can be disposed on a second portion of the substrate that is different from the first portion of the substrate.

In some embodiments, a portion of the antenna 120 can be disposed on the first major surface 112 of the substrate and another portion of the antenna 120 can be disposed on the second major surface 114. One or more spacer layers can be provided to different portions of the antenna.

In the depicted embodiments of FIGS. 1A-D, the spacer layer 140 or 140' has a frame shape with a width d corresponding to the width of the peripheral portion 113 or 113' of the substrate 110 on which the antenna 120 can be disposed. The frame shape defines a window 115 to accommodate a portion of the substrate 110 on which the sensing circuit 130 is disposed. In some embodiments, the sensing circuit 130 can be disposed at a central region of the window 115. In some embodiments, the sensing circuit 130 can be disposed on at least one of the first and second major surfaces of the substrate 110.

When the wireless sensing device 100, 100', or 100" is disposed proximate to an object (e.g., a skin of person or a fluid collection media) to measure, for example, a hydration level of the object, the sensing circuit 130 is positioned proximate to the object to measure properties of the object, while the spacer layer 140 can be positioned between the antenna and the object to prevent unpredictable performance of the antenna 120 induced by variable permittivity and conductivity in the environment (e.g., a moisture variation of the object to be tested).

The spacer layer can be made of a low-dielectric constant material and have a suitable thickness. A figure of merit of the spacer layer is defined as the ratio of thickness T of the spacer layer (in micrometers) by it's dielectric constant k (relative permittivity). The relative permittivity or dielectric constant k in the present disclosure refers to the relative permittivity of the material of a spacer layer that is expressed as a ratio of its absolute permittivity to the permittivity of vacuum. The values of the relative permittivity k are to be measured according to ASTM standard D150 at room temperature under a measuring frequency range of, for example, about 10 KHz to about 10 MHz. It is to be understood that the operational frequency of a RF sensor device may be outside of the measuring frequency range. In some embodiments, suitable low-loss dielectric materials may have monotonically and/or gradually decreasing dielectric constant with increasing frequency across a wide RF range. A spacer layer made of such low-loss dielectric materials may exhibit a lower dielectric constant at the operational frequency compared to the measured value according to ASTM standard D150, when the operational frequency is higher than the measuring frequency.

In some embodiments, the figure of merit of the spacer layer can be no less than about 20, no less than about 30, no less than about 40, no less than 50, or no less than about 100. In some embodiments, the figure of merit of the spacer layer can be in the range, for example, from about 20 to about 2000, from about 20 to about 1000, or from about 20 to about 500; from about 50 to about 2000, from about 50 to about 1000, from about 50 to about 500; or from about 100 to about 2000, from about 100 to about 1000, from about 100 to about 500.

In some embodiments, the spacer layer can be made of one or more low-dielectric constant materials including, for example, polymers, non-wovens, wovens (e.g., cotton, polymers, etc.), aerogels, glasses (e.g., fused silica, quartz, borosilicate glass, pyrex glass, etc.). Suitable polymers may include, for example, polystyrene, polyurethane, polyethylene, polypropylene, rubber, etc. Suitable low-dielectric constant materials may have a relative permittivity in the range, for example, from about 1 to about 20, from about 1.01 to about 10, from about 1.05 to about 10, from about 1.2 to about 10, from about 1.01 to about 4, from about 1.05 to about 4, from about 1.2 to about 4, from about 1.5 to about 10, or from about 1.5 to about 4.

In some embodiments, the spacer layer may have a thickness in the range, for example, from about 20 micrometers to about 2.0 cm, from about 50 micrometers to about 1.0 cm, from 100 micrometers to about 5.0 mm, from 250 micrometers to about 5.0 mm, or from 250 micrometers to about 1.0 mm. In some embodiments, the thickness of the spacer layer can be, for example, at least one time greater than, at least two times greater than, at least five times greater than, at least ten times greater, or at least twenty times greater than the thickness of the substrate 110.

In some embodiments, the spacer layer can be water-vapor resistant and configured to prevent moisture to penetrate therethrough to reach the antenna 120. In some embodiments, the spacer layer may include a barrier film, or a barrier adhesive. Exemplary barrier films or adhesives may include multilayered polymer films such as the films described in U.S. Patent Publication No. 2014/0065397 (Johnson et al.), which is incorporated herein by reference. In some embodiments, the spacer layer may have a closed cell foam structure that is water-vapor resistant. In some embodiments, the spacer layer may be further processed to be hydrophobic or water-vapor resistant. For example, the surfaces or edges of the spacer layer can be treated by suitable thermal or chemical processes to be water-vapor resistant.

The antenna 120 can have any suitable configurations designed for near-field coupling with an RF reader. The antenna 120 can be disposed on one or both sides of a substrate. In some embodiments, the antenna 120 can be a coil antenna. In some cases, the antenna 120 can have a spiral form. In some implementations, the antenna 120 can include one or more substantially concentric electrically conductive loops. In some configurations, the antenna can have a length between first and second ends, the length being less than, for example, about 2 meters. A coil antenna can have an inductance based on its geometry that produces a resonance with the capacitance of the electronically connected components, generally referred to as RF components, for enhanced induced voltage for a given magnetic field strength near the frequency of the RF reader.

In some embodiments, the antenna 120 may have an inductance based on its geometry that produces a first resonance with a first capacitance of the RF component 132 and a second resonance with a second capacitance of the RF component 132. The second resonance may be more closely matched with the frequency of an RF reader (e.g., RF reader 104 in FIG. 1E), coupling more energy into the wireless sensing device 100 due to the increased induced voltage for a given reader magnetic field strength when resonance frequency more closely matched with the RF reader frequency.

In the depicted embodiment of FIG. 1A, the sensing circuit 130 includes the RF component 132 electrically coupled to the antenna 120. In some cases, the RF component 132 can perform modulation and demodulation according to the standards, ISO 14443A, ISO 15693, or other standard or proprietary communication protocols. The sensing circuit 130 further includes a heating element 134 and a sensing element 136 thermally coupled to the heating element 134 and configured to generate a sensor signal (e.g., sensing a temperature of the heating element 134). The RF component 132 can be functionally connected to the sensing element to receive the sensor signal and communicate the sensor signal with an external device via the antenna 120.

In some implementations, the RF component 132, which may include components of a transceiver and/or a control circuit, may be configured to contain a tunable or switchable capacitance to produce the at least two values of capacitance (i.e., the first capacitance, the second capacitance), or may contain circuitry for controlling an external variable capacitance, or may contain circuitry to allow one or more external capacitance elements to be switched in or out of the circuit.

In some embodiments, the heating element 134 and the sensing element 136 can be components of an integrated circuit. In some embodiments, the sensing element 136 may be a thermal sensor that detects measurable changes in an electrical property, an optical property, an acoustic property, or the like, in response to temperature changes.

In some embodiments, the sensing circuit 130 can be a hydration sensor configured to measure a hydration level of an object when the hydration sensor is disposed proximate to the object. The sensing circuit 130 can include one or more components including, for example, a transceiver, control circuit, an energy harvesting device, an energy storage device, thermal source, a sensor, etc. It is to be understood that the sensing circuit 130 can be any suitable types of sensors for sensing physical or chemical properties of an object to be measured.

In some embodiments, one or more of the antenna 120 and the sensing circuit 130 may be components of a radio frequency identification (RFID) tag. RFID tags on flexible and/or stretchable substrates are described in more details in U.S. Patent Application No. 62/031,581, entitled "RFID Tag on Stretchable Substrate" and filed on Jul. 31, 2014, and U.S. Patent Application No. 62/031,603, entitled "RFID Tag on Flexible Substrate" and filed on Jul. 31, 2014, the entirety of which are incorporated herein by reference.

Figure 1C:
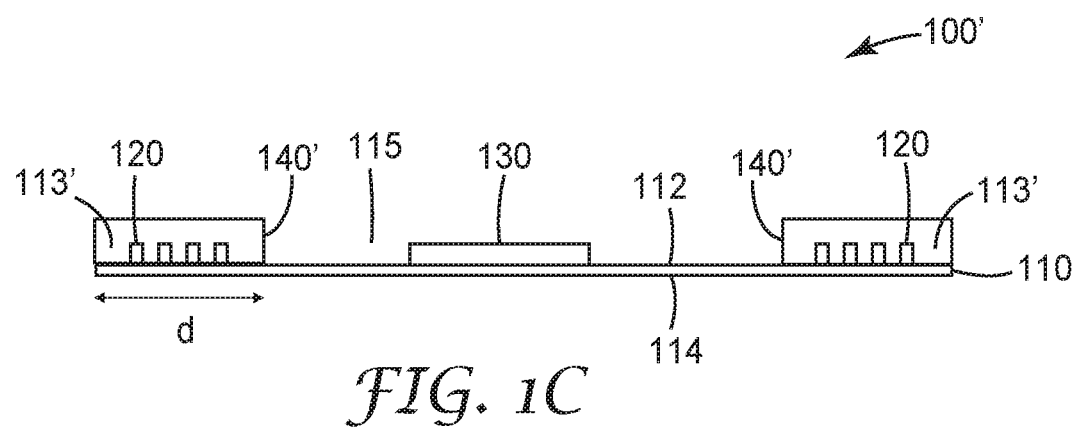
FIG. 1C illustrates a cross-sectional view of the wireless sensing device of FIG. 1A, according to another embodiment.
Figure 1D:
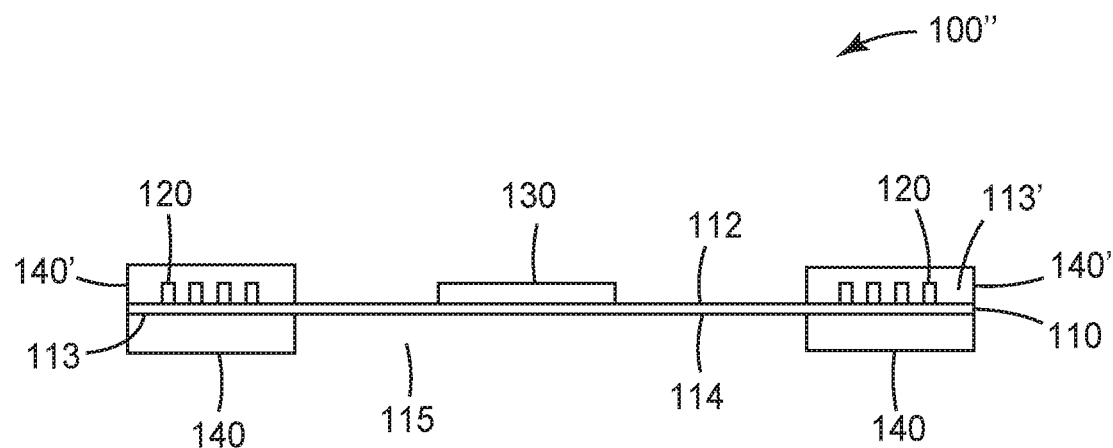
FIG. 1D illustrates a cross-sectional view of the wireless sensing device of FIG. 1A, according to another embodiment.
Figure 1E:
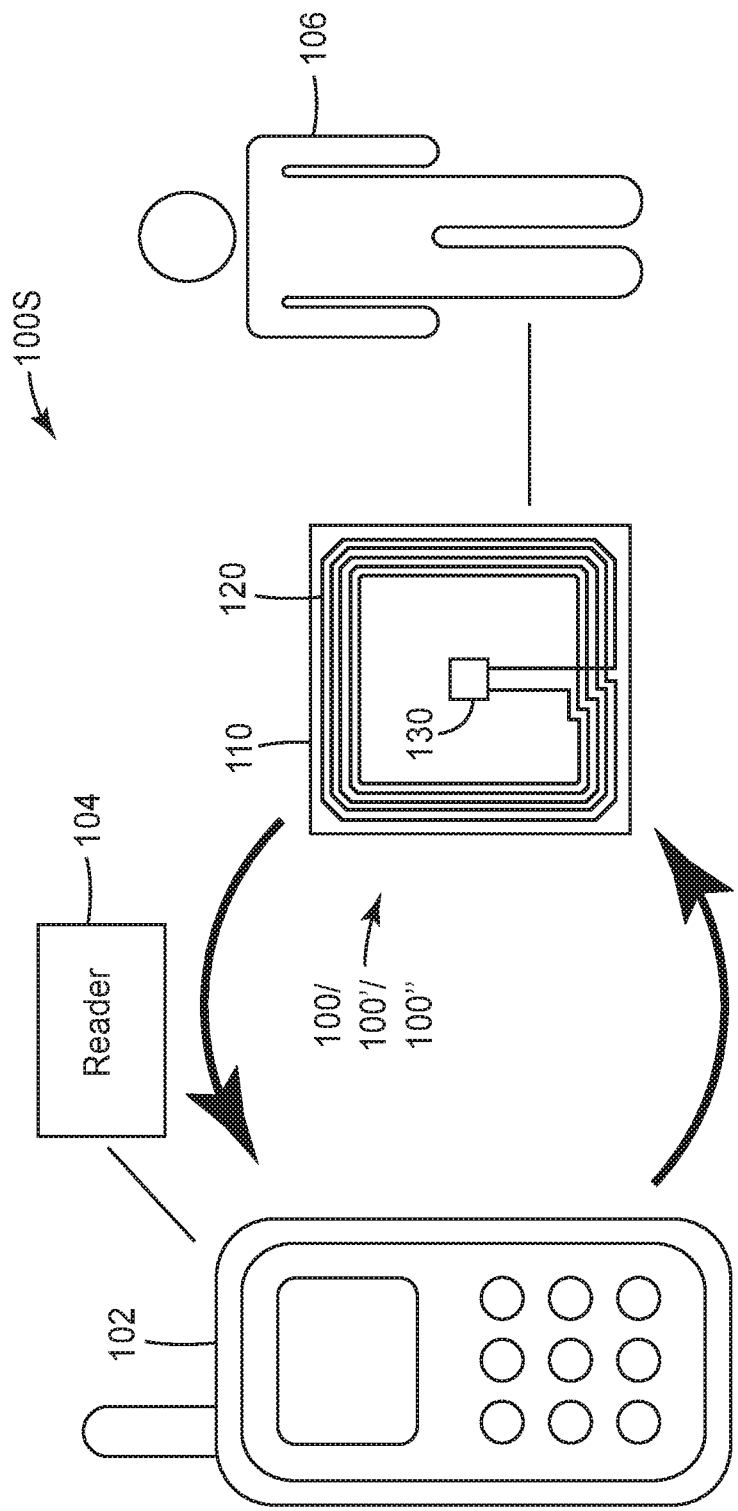
FIG. 1E illustrates a simplified schematic view of a hydration sensing system including the wireless sensing device of FIG. 1A, according to one embodiment.

FIG. 1E illustrates one embodiment of hydration sensing system 100S. The hydration sensing system 100S includes a computing device 102, a reader 104 and the wireless sensing device 100, which can be disposed in thermal contact with the skin of a person 106 or can be used to determine liquid content of a material. In some cases, the reader 104 is connected to or integrated with the computing device 102. The computing device 102 can include one or more processors, microprocessors, computers, servers, and other peripheral devices. The wireless sensing device 100, 100', or 100" can use any one or combination of the wireless sensing device configurations described in the present disclosure.

In the embodiment illustrated, the wireless sensing device includes the substrate 110, the sensing circuit 130, the antenna 120 disposed on the substrate 110 and electronically coupled to the sensing circuit 130. In some embodiments, when the sensing circuit 130 is thermally coupled to a target area, the sensing circuit 130 can sense a time variation of the target area temperature, and wirelessly transmit the sensed time variation of the temperature. The reader 104 is configured to receive the sensor signal and the computing device 102 is configured to determine a hydration indicator indicative of hydration level based on the sensed time variation of the target area temperature. In some embodiments, the wireless sensing device can include a processor to determine a hydration indicator indicative of hydration level based on the sensed time variation of the temperature.

Figure 2A:
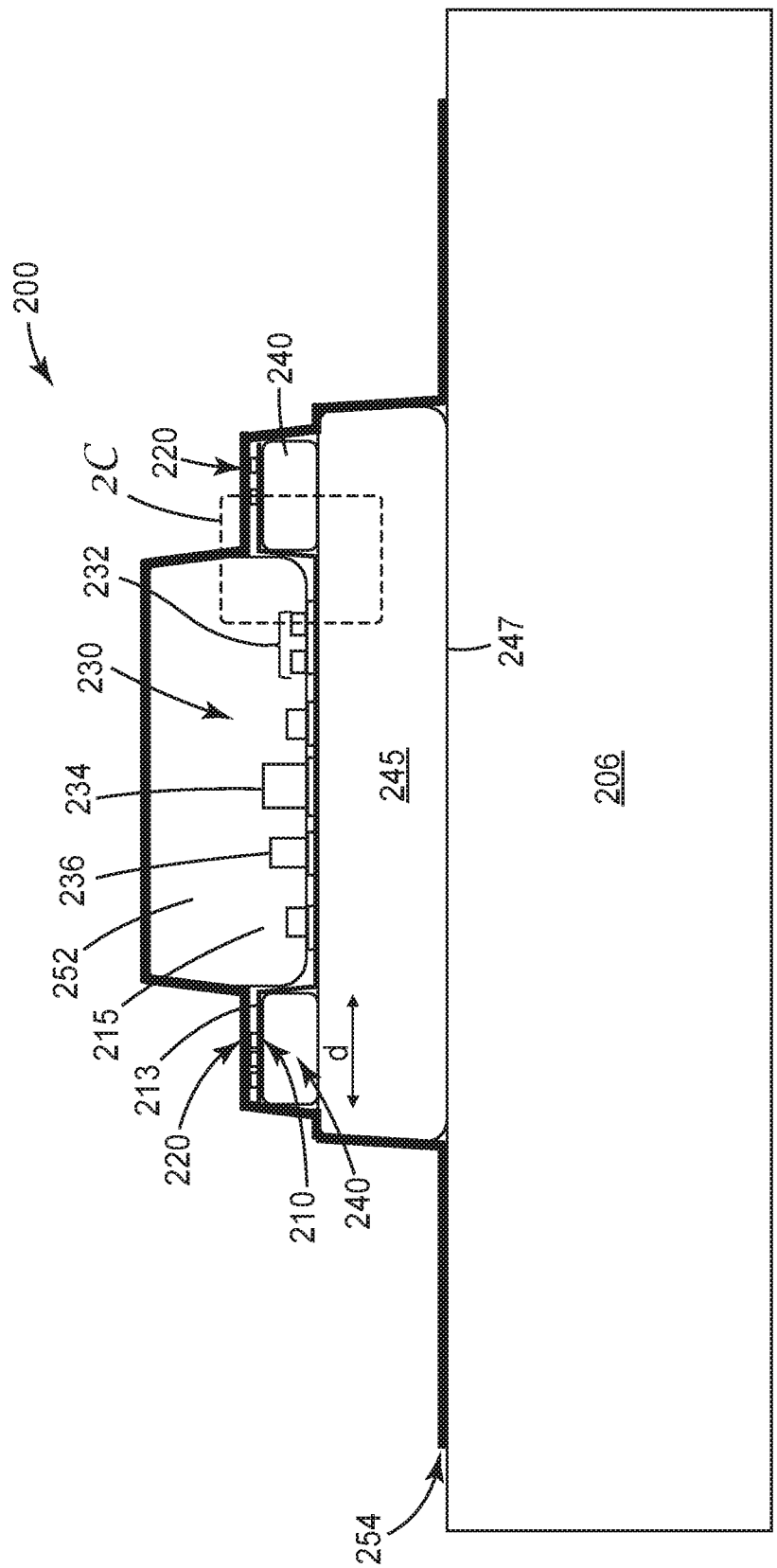
FIG. 2A illustrates a cross-sectional view of a wireless sensing device, according to one embodiment.
Figure 2B:
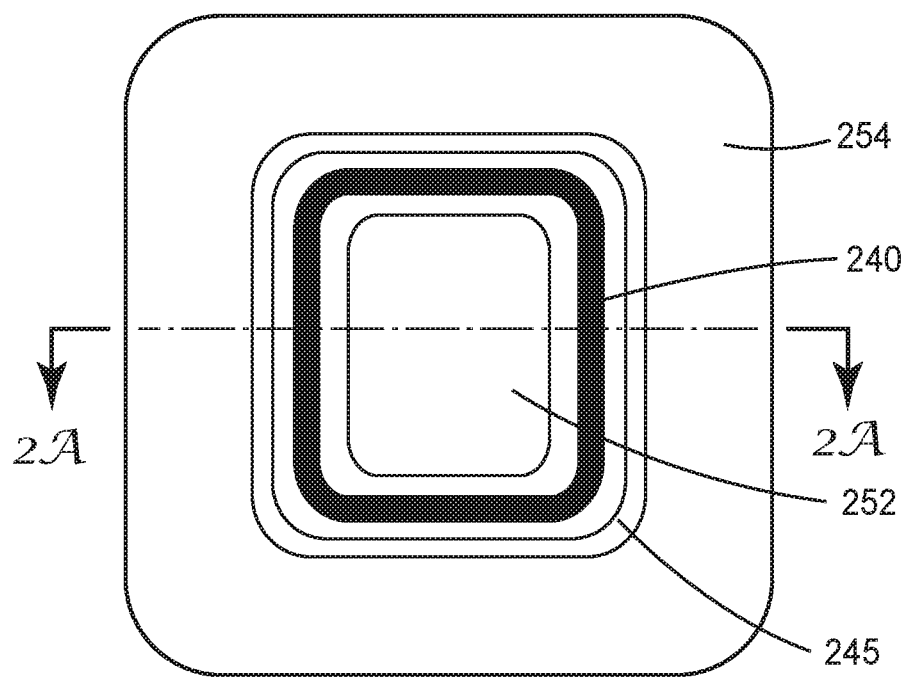
FIG. 2B illustrates a top view of the wireless sensing device of FIG. 2A.
Figure 2C:
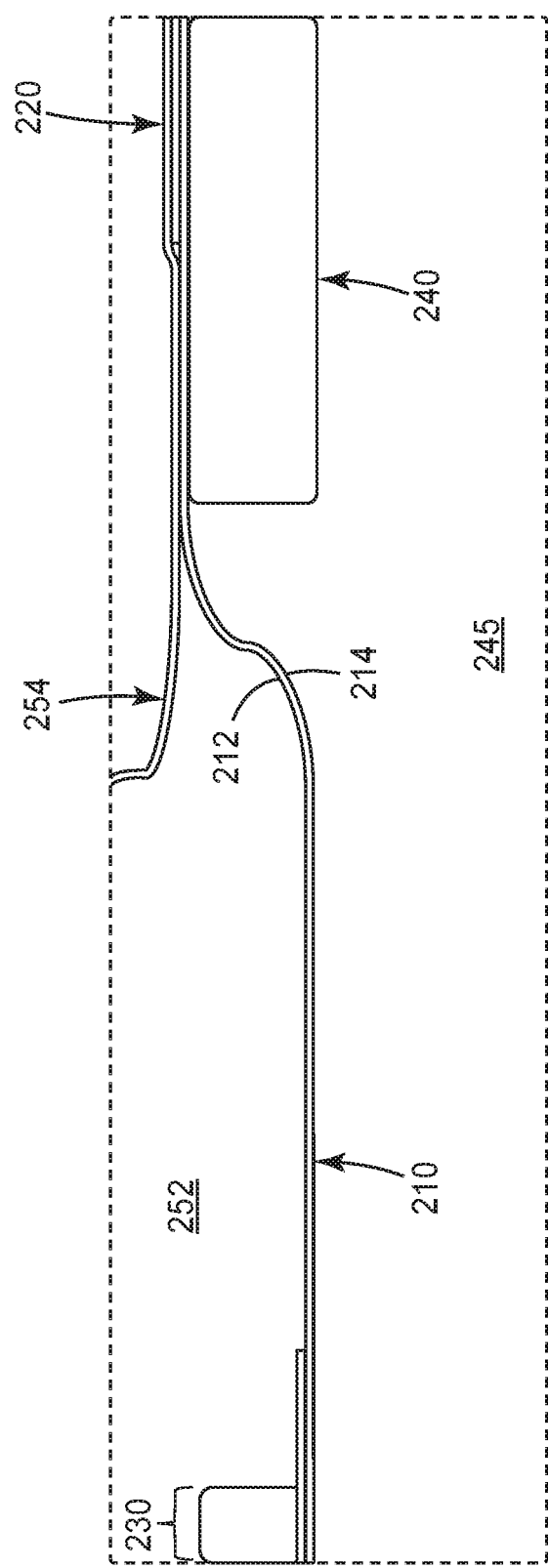
FIG. 2C illustrates an enlarged portion of the wireless sensing device of FIG. 2A.

FIG. 2A illustrates a cross-sectional view of a wireless sensing device 200, according to one embodiment. FIG. 2B illustrates a schematic top view of the wireless sensing device 200. FIG. 2C illustrates an enlarged portion view of the wireless sensing device 200. The wireless sensing device 200 is disposed on an object 206 (e.g., the skin of a person) and designed to measure a hydration level of the object 206.

The wireless sensing device 200 includes a substrate 210, an antenna 220, a sensing circuit 230 electronically coupled to the antenna 220, and a spacer layer 240. The substrate 210 has a first major surface 212 and a second major surface 214 opposite to the first major surface 212 (see FIG. 2C). The antenna 220 is disposed on a peripheral portion 213 of the first major surface 212. The sensing circuit 230 is disposed on the first major surface 212 and at least partially surrounded by the antenna 220.

In the depicted embodiment of FIG. 2A, the sensing circuit 230 includes a sensor 232 configured to generate a sensor signal, a control circuit 234 electrically connected to the sensor 232, and a transceiver 236 electrically coupled to the control circuit 234 and the antenna 220.

In some embodiments, the sensor 234, also referred to as sensing element, may be a thermal sensor that has measurable changes in electrical property, optical property, acoustic property, or the like, in response to temperature changes. In some cases, electrical thermal sensors can have a response to temperature changes in electrical voltage, current, or resistance. A resistive thermal sensor has its electrical resistance dependent on temperature; typical metals are resistive thermal devices where resistance increases with temperature in a relatively linear relationship. A thermistor typically has a resistance that depends on electrical current and non-linear resistance changes in response to temperature changes. In some implementations, electrical thermal sensors may operate based on the Seebeck effect to convert a temperature difference into an electrical voltage, such as a thermocouple or thermopile.

The control circuit 234 can include one or more electronic components that are electronically connected. The control circuit 234 can include passive electronic components, for example, such as resistors, capacitors, inductors, transformers, diodes, and the like. The control circuit 234 can include active electronic components such as transistors, voltage or current sources, amplifiers, microprocessors, oscillators, analog-to-digital converters, digital-to-analog converters, phase-locked loops, and the like. In some cases, the control circuit 234 may be formed into an integrated circuit or include an integrated circuit. A microprocessor may be a state machine with relatively simple digital logic to move among two or more states in a pre-defined manner, or a microcontroller comprised of an instruction set, digital processing blocks, memory, firmware, and peripherals such as clocks, memory controllers, and data converters. In some cases, the control circuit 234 may include a microprocessor and a memory storing a unique identifier. In some embodiments, one or more of the control circuit 234, the transceiver 236, the sensor 232 and the antenna 220 may be components of a radio frequency identification (RFID) tag.

The transceiver 236 can include a transmitter element and/or a receiver element. A transmitter element includes one or more electromagnetic or electroacoustic transducers, and electronic components to filter, amplify, and modulate one or more signals. A receiver element comprises one or more electromagnetic or electroacoustic transducers that can be shared with those of the transmitter element via a switching means or can be separate from those of the transmitter element, and electronics to filter, amplify and demodulate one or more signals from the received energy. An electromagnetic transducer can be an antenna, which can be designed to radiate electromagnetic fields from input electrical signals and absorb electromagnetic fields into electrical signals, or can be designed to couple with stored energy in electromagnetic near fields, or a combination of both radiation and near-field coupling. An electromagnetic transducer can also be a light-emitting diode or other optical source, or a photodiode or other optical detector. An electroacoustic transducer can be a loudspeaker or other acoustic source, or a microphone or other acoustic detector. Electromagnetic and/or electroacoustic transducers can be combined into a single element that is capable of bidirectional transduction from electrical signals to electromagnetic or acoustic energy, and from electromagnetic or acoustic energy to electrical signals.

The wireless sensing device 200 further includes an absorption element 245 that can be a layer of fluid collection media to absorb liquid, such as sweat, wound exudate, condensate, perspiration, oil, or the like. The absorption element 245 can be in thermal contact with one or more components of the sensing circuit 230.

In some embodiments, the sensor 232 may include a thermal source (e.g., the heating element 134 in FIG. 1A) in thermal contact with the absorption element 245. In some cases, the absorption element 245 and the thermal source/sensor 232 are disposed proximate to each other and form thermal contact. In other cases, the absorption element 245 and the thermal source/sensor 232 can be in physical, direct contact. In some cases, the thermal source/sensor 232 is disposed on or at least partially in the absorption element 245.

In the depicted embodiment of FIG. 2A, the substrate 210 along with the antenna 220 and the sensing circuit 230 disposed thereon is disposed on the absorption element 245. The spacer layer 240 is positioned between the antenna 220 and the absorption element 245 to physically separate the antenna 220 from the absorption element 245.

The spacer layer 240 has a frame shape with a width d corresponding to the width of the peripheral portion 213 of the substrate 210 on which the antenna 220 is disposed. The frame shape defines a window region 215 to accommodate a portion of the substrate 210 on which the sensing circuit 230 is disposed. The portion of the substrate 210 along with the sensing circuit 230 disposed thereon is directly disposed on the absorption element 245 such that the sensor 232 can measure physical or chemical properties (e.g., a hydration level) of the absorption element 245.

The absorption element 245 may include absorption material(s), for example, such as porous material, a natural or synthetic sponge, water-absorbing gel, superabsorbent polymer, a form, a gauze, a non-woven patch, or the like. Sponges may be made from cellulose, polyester or other polymers. Superabsorbent polymers may include, for example, polyacrylate/polyacrylamide copolymers, polyvinyl alcohol copolymers, etc.

The wireless sensing device 200 further includes electrically insulating media 252 to cover the sensing circuit 230 at the window region 215. The insulating media 252 can provide protection for the sensing circuit 232 disposed at the window region 215. A cover film 254 wraps the wireless sensing device 200 including the insulating media 252, the antenna 220, the spacer layer 240 and the absorption element 245, and attaches the wireless sensing device 200 onto an object 206 (e.g., a human skin) to be tested. In some embodiments, the cover film 254 may include an adhesive layer (e.g., pressure sensitive adhesive or PSA), and a release liner. When the release liner is removed from the cover film 254, a peripheral portion of the cover film 254 can attach to the object to press the absorption element 245 against the object to form a fluid collection interface 247 therebetween.

FIG. 3A illustrates a cross-sectional view of a wireless sensing device 300, according to another embodiment. FIG. 3B illustrates a schematic top view of the wireless sensing device 300. The wireless sensing device 300 is disposed on the object 206 and designed to measure physical or chemical properties of the object 206.

Similar to the wireless device 200 of FIG. 2A, the wireless sensing device 300 includes the substrate 210, the antenna 220, and the sensing circuit 230 electronically coupled to the antenna 220. The antenna 220 is disposed on a peripheral portion 213 of the substrate 210. The sensing circuit 230 is disposed on the substrate 210 at the window region 215. The sensing circuit 230 includes the sensor 232 configured to generate a sensor signal, the control circuit 234 electrically connected to the sensor 232, the transceiver 236 electrically coupled to the control circuit 234 and the antenna 220.

The wireless sensing device 300 further includes a spacer layer 240*a*. The spacer layer 240*a* has a frame shape with a width d corresponding to the width of the peripheral portion 213 of the substrate 210 on which the antenna 220 is disposed. The frame shape defines the window region 215 to accommodate a portion of the substrate 210 on which the sensing circuit 230 is disposed. The portion of the substrate 210 along with the sensing circuit 230 disposed thereon is directly disposed on the absorption element 245 such that the sensor 232 can measure physical or chemical properties (e.g., a hydration level) of the absorption element 245.

In the depicted embodiment of FIGS. 3A-B, the spacer layer 240*a* has a ribbed structure including a base 12, and multiple ribs 14 extending from the base 12 and separated by gaps therebetween. The base 12 is disposed on the absorption element 245. The peripheral portion 213 of the substrate 210 is supported by the distal ends of the ribs 14. The gaps between adjacent ribs can accommodate air which can further decrease the relative permittivity of the spacer layer 240*a*. The spacer layer 240*a* can be made of the same materials for the spacer layer 240 in FIG. 2A. In some embodiments, the spacer layer 240*a* can be a ribbed elastomer. The spacer layer 240*a* can be any one of the spacer layers described herein, such as the spacer layer 140, 140' in FIGS. 1B-D, and the spacer layer 240 in FIG. 2A.

Figure 4:
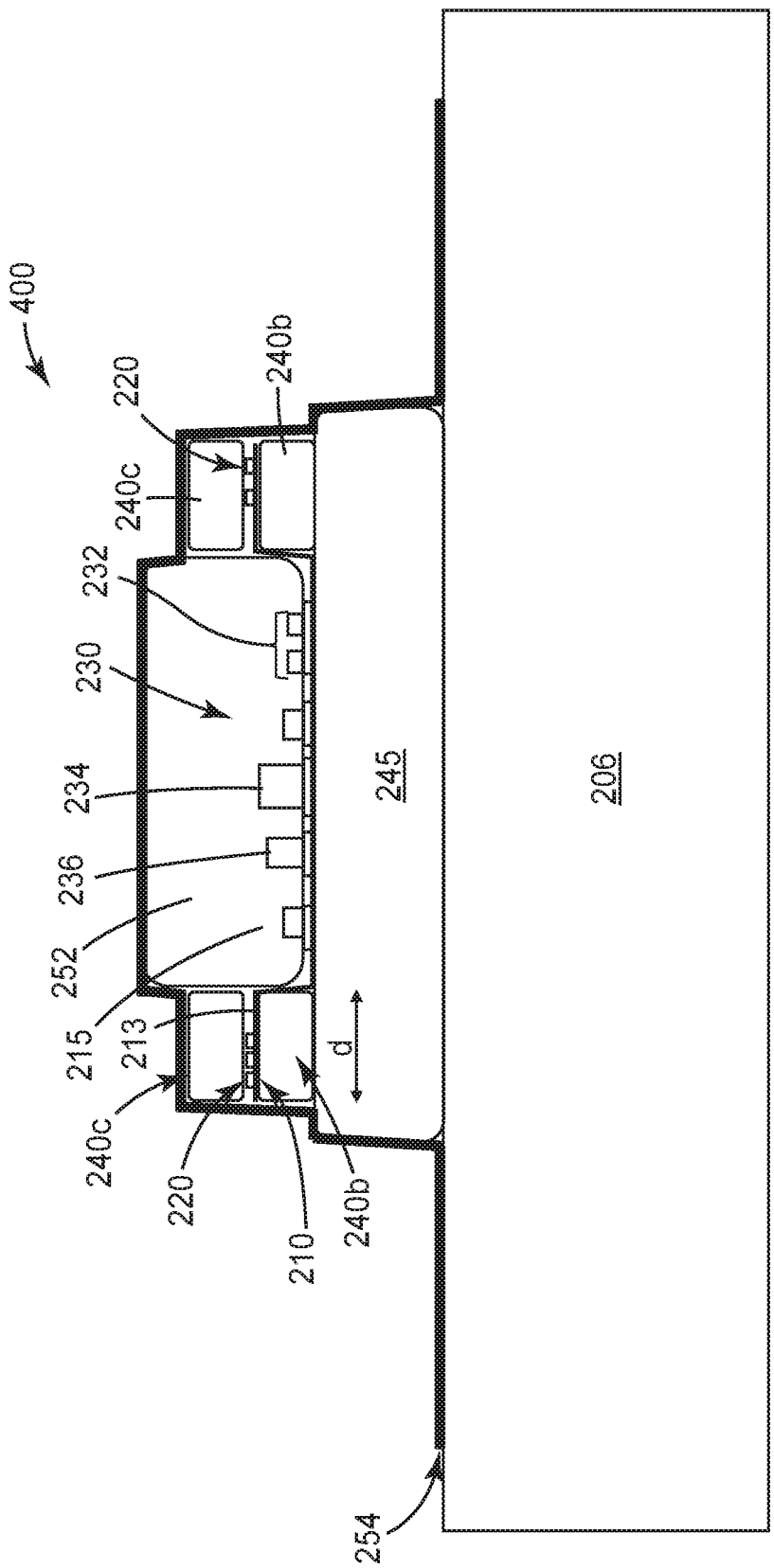
FIG. 4 illustrates a cross-sectional view of a wireless sensing device, according to another embodiment.

FIG. 4 illustrates a cross-sectional view of a wireless sensing device 400, according to another embodiment. The wireless sensing device 400 is disposed on the object 206 and designed to measure physical or chemical properties of the object 206.

Similar to the wireless device 200 of FIG. 2A, the wireless sensing device 400 includes the substrate 210, the antenna 220, and the sensing circuit 230 electronically coupled to the antenna 220. The antenna 220 is disposed on the peripheral portion 213 of the substrate 210. The sensing circuit 230 is disposed on the substrate 210 at the window region 215. The sensing circuit 230 includes the sensor 232 configured to generate a sensor signal, the control circuit 234 electrically connected to the sensor 232, the transceiver 236 electrically coupled to the control circuit 234 and the antenna 220.

The wireless sensing device 400 further includes a first spacer layer 240*b* and a second spacer layer 240*c*. The first spacer layer 240*b* is disposed between the peripheral portion 213 of the substrate 210 and the absorption element 245. The second spacer layer 240*c* is disposed on the peripheral portion 213 of the substrate 210, on the side opposite to the first spacer layer 240*b*. The first and/or the second spacer layers 240*b* and 240*c* can be any one of the spacer layers described herein, such as the spacer layer 140, 140' in FIGS. 1B-D, the spacer layer 240 in FIG. 2A, and the spacer layer 240*a* in FIG. 3A.

Figure 5:
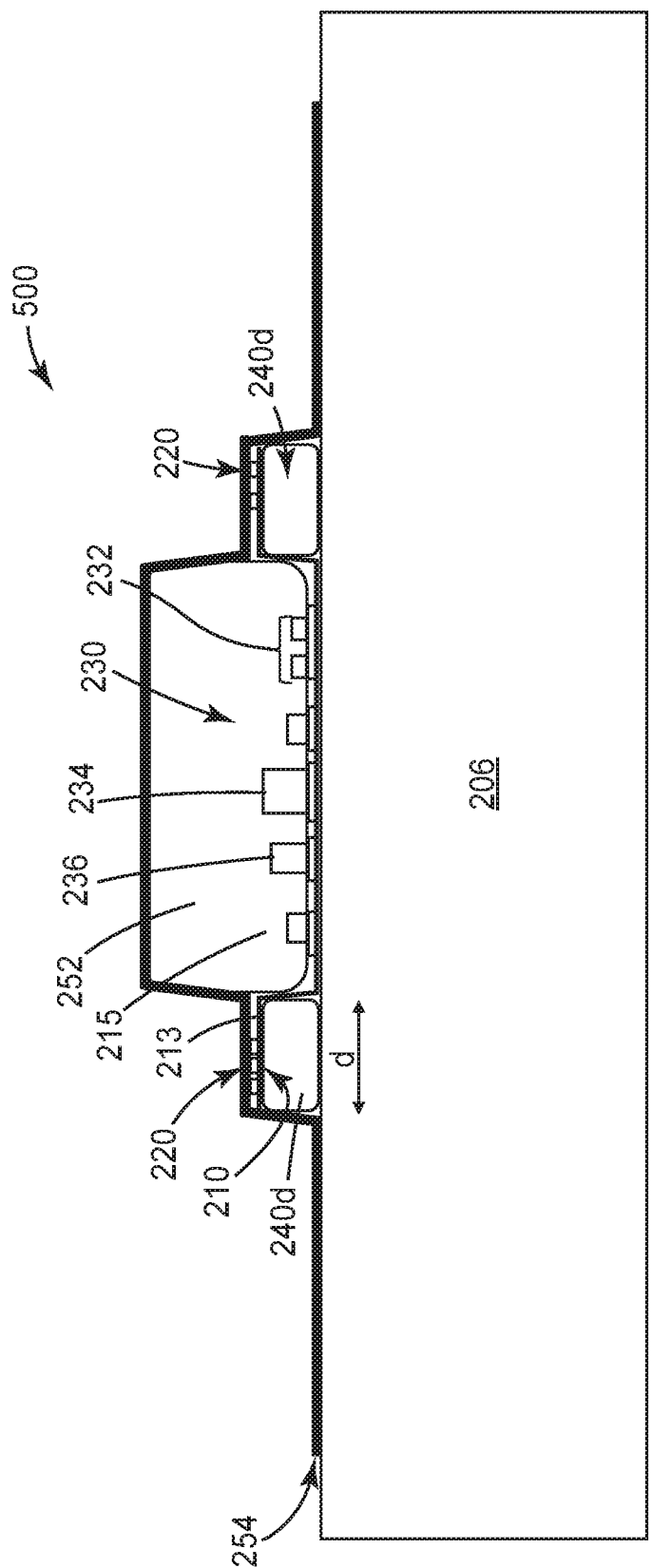
FIG. 5 illustrates a cross-sectional view of a wireless sensing device, according to another embodiment.

FIG. 5 illustrates a cross-sectional view of a wireless sensing device 500, according to another embodiment. The wireless sensing device 500 is disposed on the object 206 and designed to measure physical or chemical properties of the object 206.

Similar to the wireless device 200 of FIG. 2A, the wireless sensing device 500 includes the substrate 210, the antenna 220, and the sensing circuit 230 electronically coupled to the antenna 220. The substrate 210 along with the sensing circuit 230 disposed thereon is directly disposed on the object 206.

The wireless sensing device 500 further includes a spacer layer 240*d* disposed between the peripheral portion 213 of the substrate and the object 206. The spacer layer 240*d* can be any one of the spacer layers described herein, such as the spacer layer 140, 140' in FIGS. 1B-D, the spacer layer 240 in FIG. 2A, the spacer layer 240*a* in FIG. 3A, and the spacer layers 240*b-c* in FIG. 4.

Figure 6:
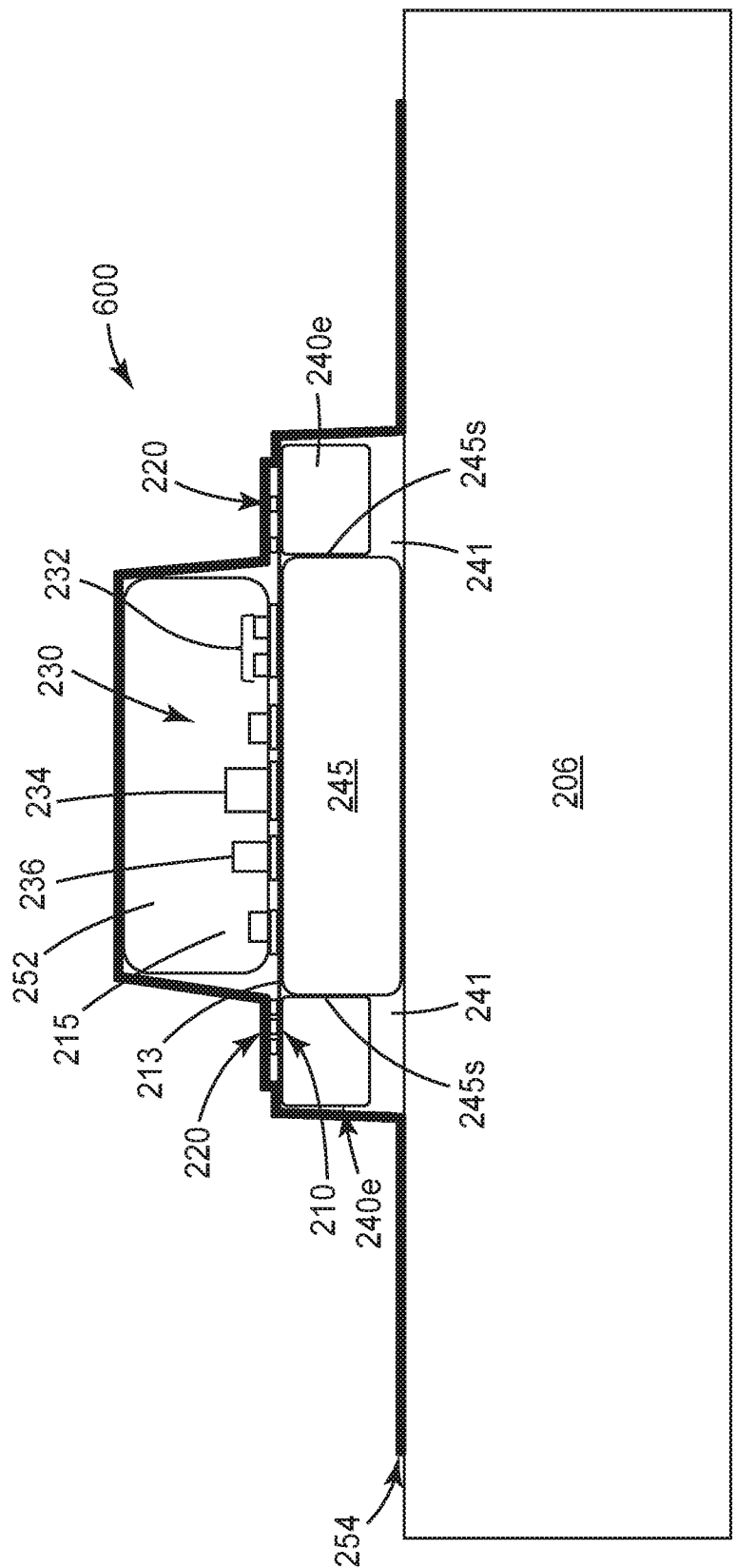
FIG. 6 illustrates a cross-sectional view of a wireless sensing device, according to another embodiment.

FIG. 6 illustrates a cross-sectional view of a wireless sensing device 600, according to another embodiment. The wireless sensing device 600 is disposed on the object 206 and designed to measure physical or chemical properties of the object 206.

Similar to the wireless device 200 of FIG. 2A, the wireless sensing device 600 includes the substrate 210, the antenna 220, and the sensing circuit 230 electronically coupled to the antenna 220. The antenna 220 is disposed on a peripheral portion 213 of the substrate 210. The sensing circuit 230 is disposed on the substrate 210 at the window region 215.

The wireless sensing device 600 further a spacer layer 240*e* which is attached to a side surface 245*s* of the absorption element 245. The peripheral portion 213 of the substrate 220 along with the antenna 220 disposed thereon is supported by the spacer layer 240e. The spacer layers 240e can be any one of the spacer layers described herein, such as the spacer layer 140, 140' in FIGS. 1B-D, the spacer layer 240 in FIG. 2A, the spacer layer 240a in FIG. 3A, the spacer layers 240b-c in FIG. 4, and the spacer layer 240d in FIG. 5.

In the depicted embodiment, the spacer layer 240e has a thickness less than the thickness of the absorption element 245 such that a gap region 241 can be formed between the spacer layer 240e and the object 206.

Figure 7:
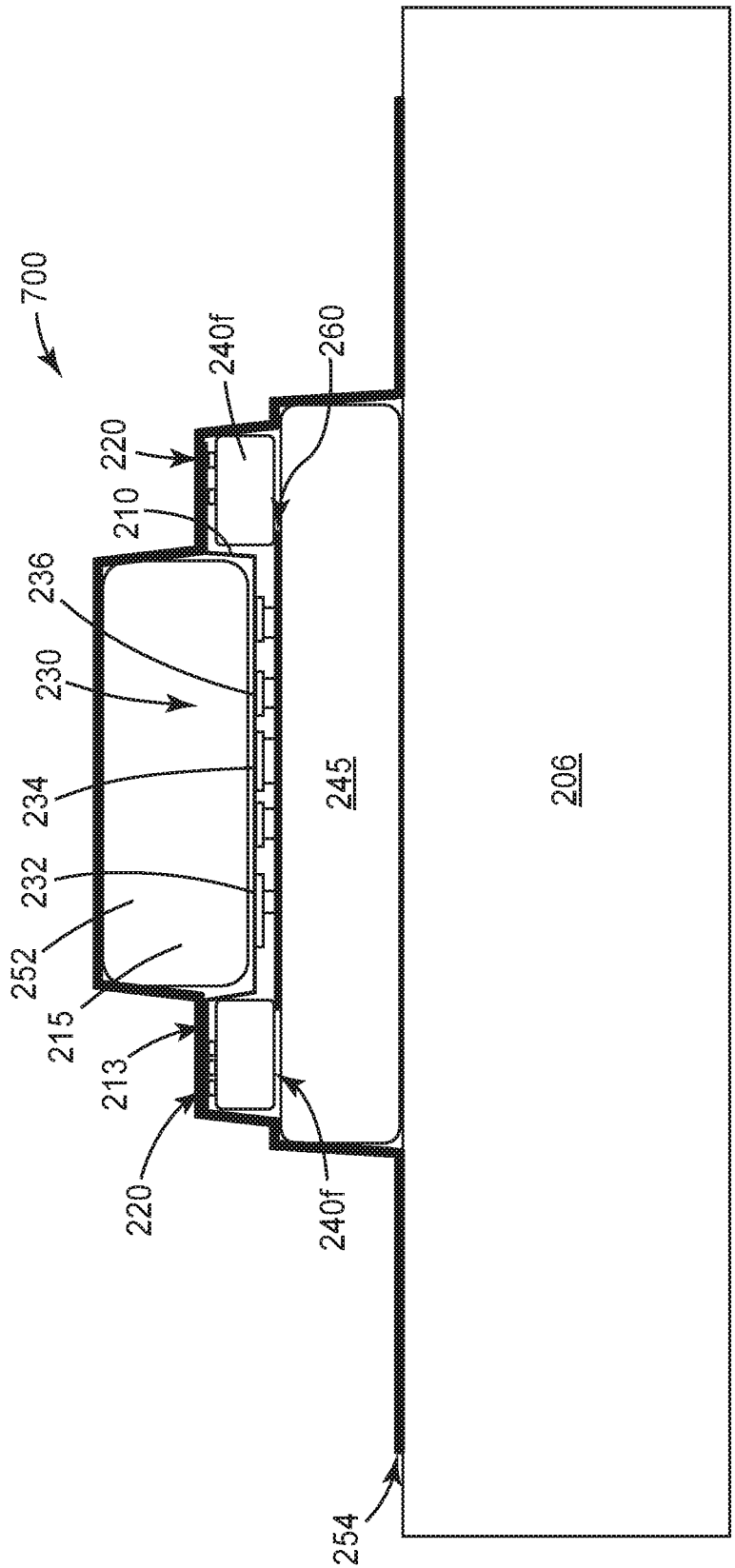
FIG. 7 illustrates a cross-sectional view of a wireless sensing device, according to another embodiment.
Figure 8A:
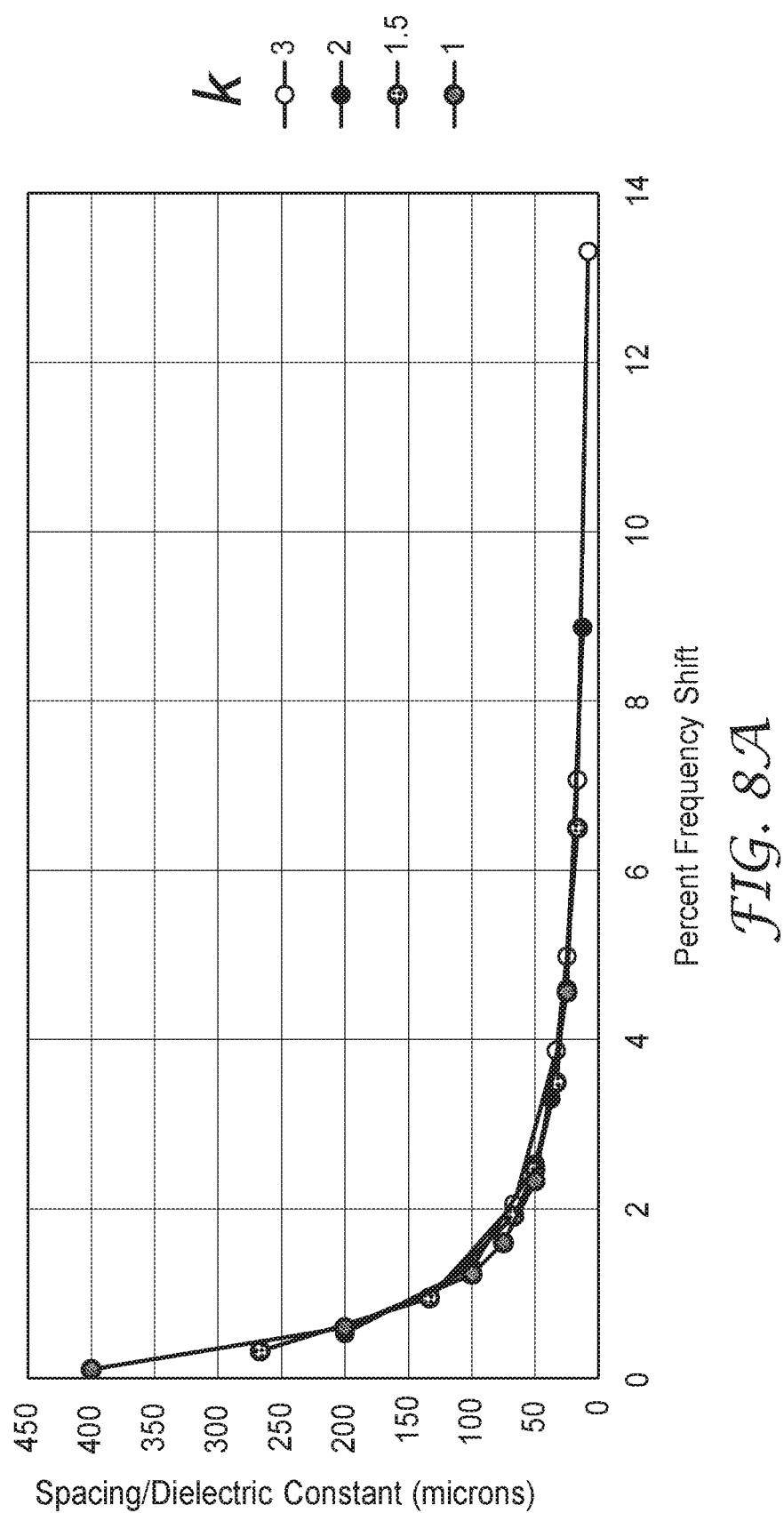
FIG. 8A illustrates a plot of the frequency shift (%) versus the ratio of the spacing and relative permittivity for the series of Examples 1.
Figure 8B:
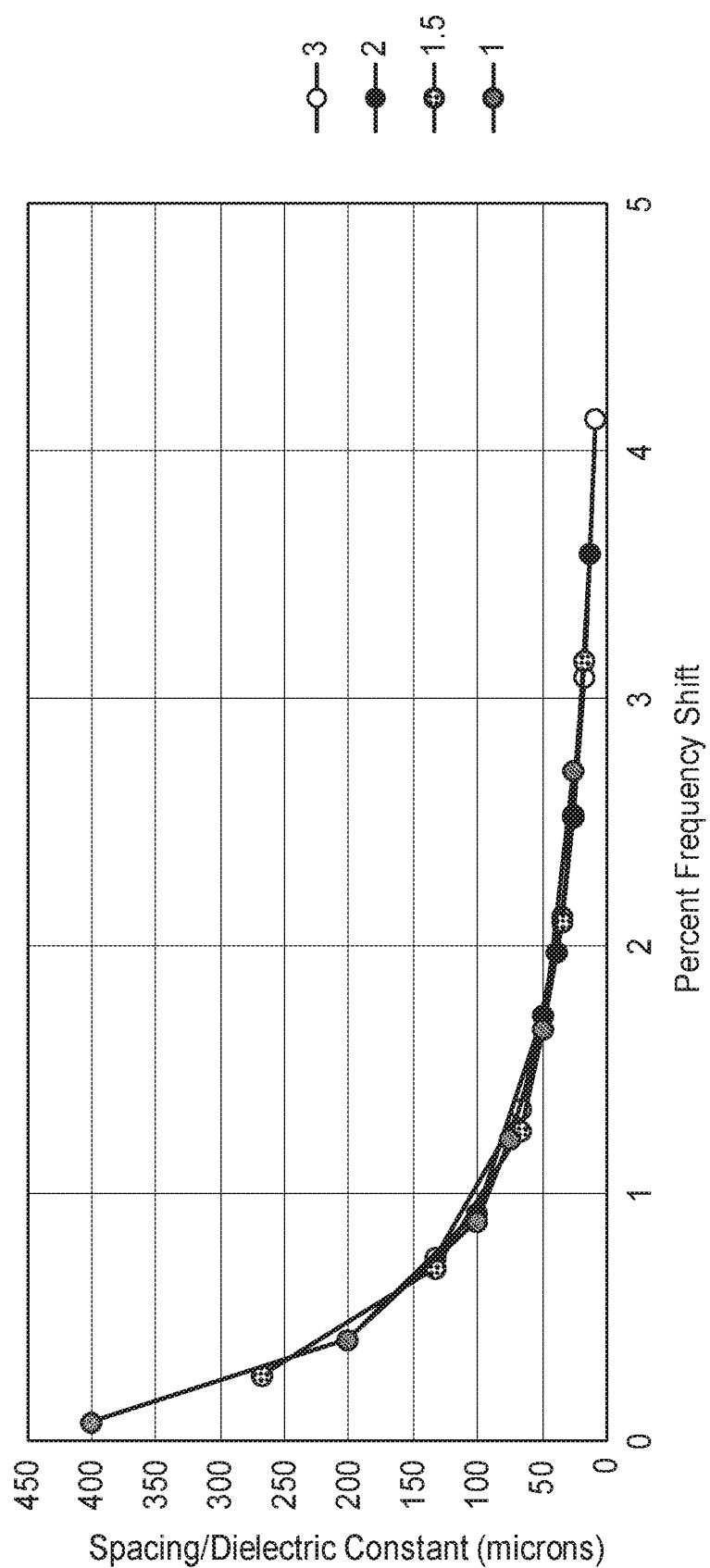
FIG. 8B illustrates a plot of the frequency shift (%) versus the ratio of the spacing and relative permittivity for the series of Examples 2.
Figure 8C:
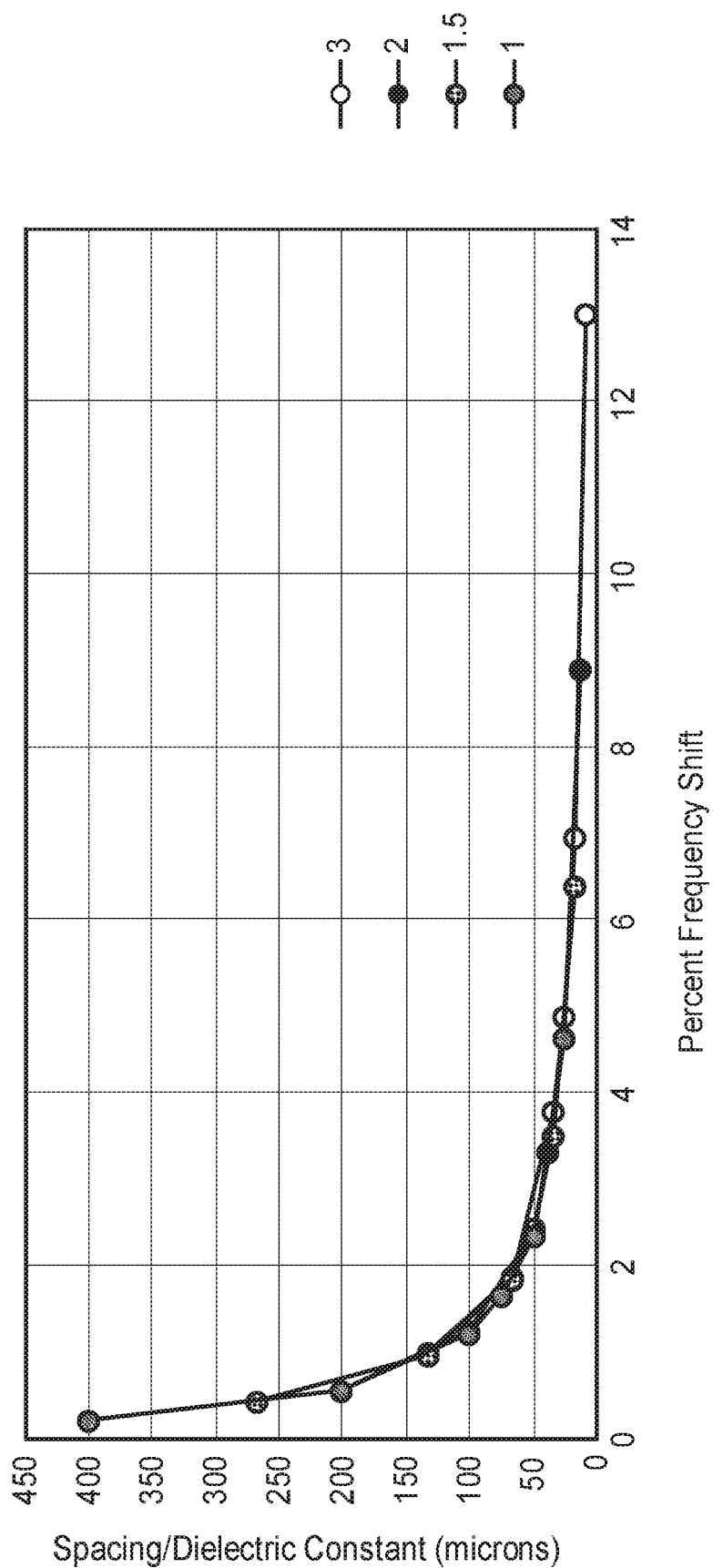
FIG. 8C illustrates a plot of the frequency shift (%) versus the ratio of the spacing and relative permittivity for the series of Examples 3.
Figure 8D:
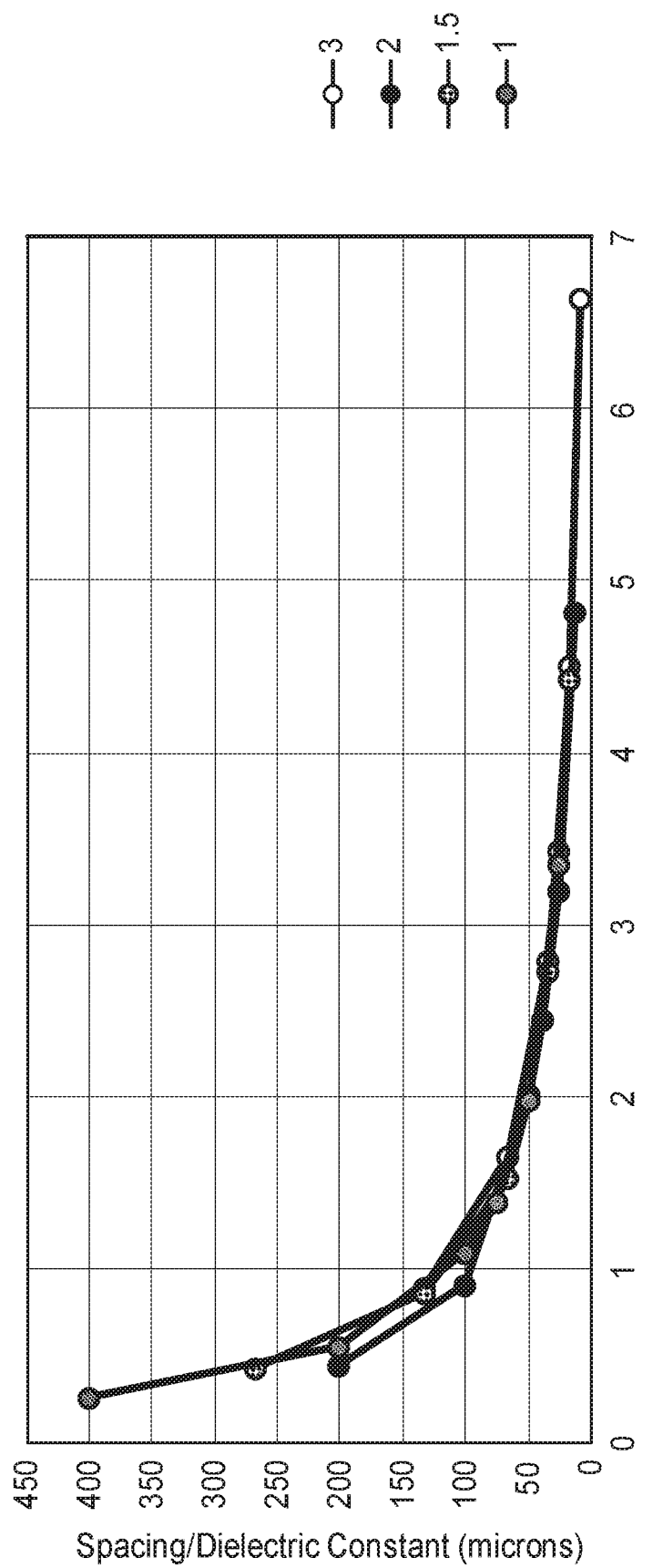
FIG. 8D illustrates a plot of the frequency shift (%) versus the ratio of the spacing and relative permittivity for the series of Examples 4.

FIG. 7 illustrates a cross-sectional view of a wireless sensing device 700, according to another embodiment. The wireless sensing device 700 is disposed on the object 206 and designed to measure physical or chemical properties of the object 206.

Similar to the wireless device 200 of FIG. 2A, the wireless sensing device 400 includes the substrate 210, the antenna 220, and the sensing circuit 230 electronically coupled to the antenna 220. The antenna 220 is disposed on the peripheral portion 213 of the substrate 210. The sensing circuit 230 is disposed on the substrate 210 at the window region 215. The sensing circuit 230 includes the sensor 232 configured to generate a sensor signal, the control circuit 234 electrically connected to the sensor 232, the transceiver 236 electrically coupled to the control circuit 234 and the antenna 220.

The wireless sensing device 700 further includes a spacer layer 240f which is disposed between the peripheral portion 213 of the substrate 210 and the absorption element 245. Different from the wireless device 200 of FIG. 2A, the substrate 210 has the components disposed thereon (e.g., the sensing circuit 230, the antenna 220, etc.) facing the object 206. The spacer layer 240f is disposed on the antenna 220 to physically separate the antenna 220 from the absorption element 245. The spacer layer 240f can be any one of the spacer layers described herein, such as the spacer layer 140, 140' in FIGS. 1B-D, the spacer layer 240 in FIG. 2A, the spacer layer 240a in FIG. 3A, the spacer layers 240b-c in FIG. 4, the spacer layer 240d in FIG. 5, and the spacer layer 240e in FIG. 6.

The wireless sensing device 700 further includes a barrier layer 260 that is disposed at the window region 215 to physically separate the sensing circuit 230 from the absorption element 245.

Unless otherwise indicated, all numbers expressing quantities or ingredients, measurement of properties and so forth used in the specification and embodiments are to be understood as being modified in all instances by the term "about." Accordingly, unless indicated to the contrary, the numerical parameters set forth in the foregoing specification and attached listing of embodiments can vary depending upon the desired properties sought to be obtained by those skilled in the art utilizing the teachings of the present disclosure. At the very least, and not as an attempt to limit the application of the doctrine of equivalents to the scope of the claimed embodiments, each numerical parameter should at least be construed in light of the number of reported significant digits and by applying ordinary rounding techniques.

Exemplary embodiments of the present disclosure may take on various modifications and alterations without departing from the spirit and scope of the present disclosure. Accordingly, it is to be understood that the embodiments of the present disclosure are not to be limited to the following described exemplary embodiments, but is to be controlled by the limitations set forth in the claims and any equivalents thereof.

Listing of Exemplary Embodiments

Exemplary embodiments are listed below. It is to be understood that any one of embodiments 1-20, 21-35, 367 and 38-39 can be combined.

Embodiment 1 is a radio-frequency (RF) sensor device comprising:
 a substrate;
 an antenna having at least a portion disposed on a first portion of the substrate;
 a sensor disposed on a second portion of the substrate, the sensor being at least partially surrounded by the antenna, the sensor including an RF component electrically coupled to the antenna; and
 a spacer layer attached to the first portion of the substrate adjacent to the antenna,
 wherein the spacer layer has a thickness T, a relative permittivity k, and a figure of merit defined as the ratio of T (in micrometers) by k, the spacer layer has the figure of merit no less than 20 (micrometers).

Embodiment 2 is the RF sensor device of embodiment 1, wherein the spacer layer has the figure of merit no less than 50 (micrometers).

Embodiment 3 is the RF sensor device of embodiment 1 or 2, wherein the relative permittivity of the spacer layer is in the range from about 1.01 to about 4, and the thickness of the spacer layer is in the range from about 250 micrometers to about 1.0 mm.

Embodiment 4 is the RF sensor device of any one of embodiments 1-3, wherein the spacer layer comprises one or more low-dielectric constant materials including one or more of polymers, non-woven materials, woven materials, aerogels, or glasses.

Embodiment 5 is the RF sensor device of any one of embodiments 1-4, wherein the spacer layer is water-vapor resistant and configured to prevent moisture to penetrate therethrough to reach the antenna.

Embodiment 6 is the RF sensor device of any one of embodiments 1-5, wherein the spacer layer has a frame shape with a width corresponding to the width of the first portion of the substrate, the frame shape defining a window to accommodate a portion of the substrate on which the sensor is disposed.

Embodiment 7 is the RF sensor device of any one of embodiments 1-6, wherein the spacer layer includes a ribbed structure.

Embodiment 8 is the RF sensor device of any one of embodiments 1-7, wherein the spacer layer includes a closed-cell foam.

Embodiment 9 is the RF sensor device of any one of embodiments 1-8, wherein the spacer layer is disposed on the antenna to cover at least a portion of the antenna.

Embodiment 10 is the RF sensor device of any one of embodiments 1-9, wherein the spacer layer is disposed on the side of the substrate opposite to the antenna.

Embodiment 11 is the RF sensor device of any one of embodiments 1-10, wherein the sensor is a hydration sensor configured to measure a hydration level of an object when the hydration sensor is disposed proximate to the object.

Embodiment 12 is the RF sensor device of embodiment 11, further comprising an absorption element, wherein at least a portion of the substrate is disposed on the absorption element media such that the hydration sensor is disposed proximate to the absorption element.

Embodiment 13 is the RF sensor device of embodiment 11 or 12, wherein the spacer layer is sandwiched between the first portion of the substrate and the absorption element.

Embodiment 14 is the RF sensor device of any one of embodiments 11-13, wherein the spacer layer is disposed around a periphery of the absorption element.

Embodiment 15 is the RF sensor device of any one of embodiments 11-14, further comprising a barrier layer to separate the hydration sensor from the absorption element.

Embodiment 16 is the RF sensor device of any one of embodiments 10-15, wherein the hydration sensor further comprises a thermal source element electrically coupled to the RF element to change a thermal condition of a target area.

Embodiment 17 is the RF sensor device of embodiment 16, wherein the hydration sensor further comprises a sensing element thermally coupled to the thermal source element to sense a temperature of the thermal source.

Embodiment 18 is the RF sensor device of any one of embodiments 1-17, further comprising a layer of insulating media to cover the sensor disposed on the substrate.

Embodiment 19 is the RF sensor device of any one of embodiments 1-18, further comprising a cover film to wrap components disposed on the substrate.

Embodiment 20 is the RF sensor device of embodiment 19, wherein the cover film has a peripheral portion with an adhesive surface.

Embodiment 21 is a RF sensor to measure a hydration level, comprising:
  a substrate;
  an antenna having at least a portion disposed on a peripheral portion of the substrate;
  an absorption element comprising a fluid absorption material;
  a spacer layer attached to the peripheral portion of the substrate adjacent to the antenna, the spacer layer has a thickness T, a relative permittivity k, and a figure of merit defined as the ratio of T (in micrometers) by k, the spacer layer has the figure of merit no less than 20; and
  a sensor element disposed on the substrate, the sensor element being positioned proximate to the absorption element and configured to measure the hydration level of the absorption element, the sensor element being at least partially surrounded by the antenna and electrically coupled to the antenna.

Embodiment 22 is the RF sensor of embodiment 21, wherein the spacer layer has a frame shape with a width corresponding to the width of the peripheral portion of the substrate, the frame shape defining a window within which the sensor element is disposed and in contact with the fluid collection media.

Embodiment 23 is the RF sensor of embodiment 21 or 22, wherein the spacer layer includes a ribbed structure.

Embodiment 24 is the RF sensor of any one of embodiments 21-23, wherein the spacer layer includes a closed-cell foam.

Embodiment 25 is the RF sensor of any one of embodiments 21-24, wherein the spacer layer is sandwiched between the substrate and the absorption element.

Embodiment 26 is the RF sensor of any one of embodiments 21-25, wherein the spacer layer is disposed around a periphery of the absorption element.

Embodiment 27 is the RF sensor of any one of embodiments 21-26, wherein the spacer layer is disposed on the antenna to cover a least a portion of the antenna.

Embodiment 28 is the RF sensor of any one of embodiments 21-27, wherein the spacer layer is disposed on the substrate at the side opposite to the antenna.

Embodiment 29 is the RF sensor of embodiment 27, further comprising a barrier layer to separate the substrate from the absorption element.

Embodiment 30 is the RF sensor of any one of embodiments 21-29, further comprising a cover layer to cover the antenna.

Embodiment 31 is the RF sensor of any one of embodiments 21-30, further comprising a layer of insulating media to cover the sensor element disposed on the substrate.

Embodiment 32 is the RF sensor of embodiment 31, further comprising a cover film to wrap components disposed on the substrate.

Embodiment 33 is the RF sensor of embodiment 32, wherein the cover film has a peripheral portion with an adhesive surface.

Embodiment 34 is the RF sensor of any one of embodiments 21-33, wherein the absorption material comprises at least one of a porous material, a natural or synthetic sponge, water-absorbing gel, and superabsorbent polymer.

Embodiment 35 is the RF sensor of any one of embodiments 21-34, wherein the relative permittivity of the spacer layer is in the range from about 1.01 to about 4, and the thickness of the spacer layer is in the range from about 250 micrometers to about 1.0 mm.

Embodiment 36 is a radio-frequency (RF) sensor device comprising:
  a substrate;
  an antenna having at least a portion disposed on a first portion of the substrate;
  a sensor disposed on a second portion of the substrate, the sensor including an RF component electrically coupled to the antenna; and
  a spacer layer attached to the first portion of the substrate adjacent to the antenna, the spacer layer being separate from the second portion of the substrate,
  wherein the spacer layer has a thickness T, a relative permittivity k, and a figure of merit defined as the ratio of T (in micrometers) by k, the spacer layer has the figure of merit no less than 20 (micrometers).

Embodiment 37 is the RF sensor device of embodiment 36, further comprising an absorption element, wherein at least a portion of the second portion of the substrate is directly disposed on the absorption element media.

Embodiment 38 is a radio-frequency (RF) sensor device comprising:
  a substrate;
  an antenna having at least a portion disposed on a peripheral portion of the substrate;
  a sensor disposed on a central portion of the substrate, the sensor including an RF component electrically coupled to the antenna; and
  a spacer layer attached to the peripheral portion of the substrate adjacent to the antenna,
  wherein the spacer layer has a thickness T, a relative permittivity k, and a figure of merit defined as the ratio of T (in micrometers) by k, the spacer layer has the figure of merit no less than 20 (micrometers).

Embodiment 39 is the RF sensor device of embodiment 38, further comprising an absorption element, wherein at least a portion of the central portion of the substrate is directly disposed on the absorption element media.

Examples

These examples are merely for illustrative purposes and are not meant to be limiting on the scope of the appended claims. All parts, percentages, ratios, etc. in the examples and the rest of the specification are by weight, unless noted otherwise.

Simulation Examples

Examples 1-4 were modeled in the Computer Simulation Technology (CST) Microwave Studio EM simulation environment using the frequency domain solver. Examples 1 and 3 have the configuration shown in FIG. 1C, and were disposed on a skin and an absorption element, respectively. Examples 2 and 4 have the configuration shown in FIG. 1B, and were disposed on the skin and the absorption element, respectively. The substrate is about 50 micrometers thick and has a relative permittivity about 3.2. The skin has a relative permittivity about 31.3 and electrical conductivity about 8.0 S/m. The absorption element has a thickness about 1.0 mm and a water model was used with the relative permittivity about 78 and the electrical conductivity about 1.59 S/m.

The values of "Resonance frequency shift (%)" were calculated as the resonance frequency difference when the antenna is positioned away from the skin or the absorption element and when the antenna is disposed on the skin or the absorption element. Table 1 below listed more details for Examples 1-4 and Comparative Examples C1-2. Examples 1-4 exhibited superior properties in stabilizing the resonant frequency of the antenna and reducing the decay in the quality factor.

TABLE 1

| | Configuration | Spacer layer k | Spacer layer T (μm) | Resonance frequency shift (%) | Quality factor - Away | Quality factor - on |
|---|---|---|---|---|---|---|
| Comparative Example C1 | w/o spacer layer; on skin | N.A. | N.A. | 6.6 | 71 | 44 |
| Example 1 | FIG. 1C; With spacer layer on skin | 1.5 | 400 | 0.3 | 61 | 47 |
| Example 2 | FIG. 1B; With spacer layer on skin | 2 | 400 | 0.5 | 67 | 56 |
| Comparative Example C2 | w/o spacer layer; on absorption element | N.A. | N.A. | 13.7 | 61 | 24 |
| Example 3 | FIG. 1C; With spacer layer on absorption element | 1.5 | 400 | 0.4 | 53 | 49 |
| Example 4 | FIG. 1B; With spacer layer on absorption element | 1.5 | 400 | 0.4 | 60 | 54 |

By varying the relative permittivity and thickness of the spacer layer, a series of Examples 1, Examples 2, Examples 3, and Examples 4 were built. Similar simulations were conducted to calculate the resonance frequency shift. FIGS. 8A-D illustrates a plot of the frequency shift (%) versus the ratio of D/k for the series of Examples 1-4, respectively, where D is the vertical spacing between the antenna and the skin or absorption element, and k is the relative permittivity of the spacer layer. For Examples 1 and 3, the vertical spacing is approximately the thickness T of the spacer layer. For Examples 2 and 4, the spacing D includes the thickness T of the spacer layer and that of the substrate.

Experimental Examples

Examples in Set 2 (Examples A and F) were fabricated according to the configuration shown in FIG. 2A. Examples in Set 3 (Examples D and E) were fabricated according to the configuration shown in FIG. 6. Comparative Examples in Set 1 (Examples B and C) were fabricated according to the configuration shown in FIG. 2A or 6, but without a spacer layer. The materials for the Examples are listed in Table 2 below.

TABLE 2

| Components | Materials |
|---|---|
| Substrate | Espanex Polyimide Laminate MC 18-25-00 CEM, Electro-Materials Inc, Eagan MN |
| Antenna | Espanex Polyimide Laminate MC 18-25-00 CEM, Electro-Materials Inc, Eagan MN |
| Spacer layer | 3M 1774W (Set 2), 3M 1772 (Set 3), 3M Company, Saint Paul, MN |
| Absorption element | 3M MSX-6916B, 3M Company, Saint Paul, MN |
| Adhesive between substrate and absorption element | 3M Tegaderm adhesive (25 μm acrylate), 3M Company, Saint Paul, MN |

The examples in Set 1 and Set 2 have a fluid-collection media area of 3.5 cm×3.0 cm. The examples in Set 3 has a reduced fluid-collection media area of 2.0×1.5 cm and it was inset inside the frame of 1772 closed-cell foam Tuning capacitors were used to set the resonant frequency of each example to be approximately equal to one another. Each example has 1 or 2 ceramic capacitors of 0402 size (1.0×0.5 mm), of NP0 type for low loss, with capacitor values as listed in the table further below.

The antenna for each example is 4 turns of copper with 0.4 mm trace width and 0.4 mm spacing between traces, and 30.6 mm×25.6 mm outer diameter. Antenna patterns were etched into copper-polyimide laminate (Espanex Polyimide Laminate MC 18-25-00 CEM, Electro-Materials Inc, Eagan, Minn.). The jumper across inner-outer antenna pads was made with a narrow gauge wire, with antenna traces underneath locally insulated by polyimide tape.

After adding the Near Field Communication (NFC) integrated circuit to each antenna (NT3H1101W0FTT from NXP Semiconductors, Eindhoven, Netherlands), the examples were tuned to have resonance frequency f0 nearly equal to one another, and in the vicinity of 13.56 MHz. To verify tuning, resonance frequency f0 and quality factor Q were measured with a Keysight E4990A impedance analyzer and a ~5 cm diameter planar reader antenna, with tags separated by ~1 cm spacing from the reader antenna and approximately centered. Quality factor Q was determined from the reflected impedance measurement as the ratio of the resonance frequency to the bandwidth (full-width at half-maximum) of the real part of impedance. Table 3 below shows tag assignments into sample sets along with each tag's tuning capacitor values, measured values of f0 and Q after assembly into each of the constructions are shown in the table below, and the nominal volume of the fluid collection media based on its MSX-6916B foam layer area and thickness.

TABLE 3

| Sample ID | Sample Set | Added tuning C (pF) | Assembled resonance f0 (MHz) | Assembled quality factor Q | Fluid-collection media volume (mL) | Targeted fluid volume for 20% fill (mL) |
|---|---|---|---|---|---|---|
| A | Set 2 | 100 + 2.2 | 13.75 | 51.5 | 2.52 | 0.504 |
| B | Set 1 | 100 | 13.74 | 51.5 | 2.52 | 0.504 |
| C | Set 1 | 100 + 1 | 13.75 | 52.5 | 2.52 | 0.504 |
| D | Set 3 | 100 + 3.3 | 13.74 | 52 | 0.72 | 0.144 |
| E | Set 3 | 100 | 13.75 | 51 | 0.72 | 0.144 |
| F | Set 2 | 100 + 1 | 13.76 | 52 | 2.52 | 0.504 |

A saline solution of 1% NaCl by weight in distilled water was prepared as the fluid for this example. The handbook value for conductivity of such a solution is 1.6 S/m. (NaCl: Sigma-Aldrich sodium chloride anhydrous Redi-Dri™ ACS reagent >99%; water: Market Pantry Distilled Water, Target Corp.)

Each example's performance was evaluated using a Voyantic Tagformance HF system using distance control kit to change the distance between the reader and the sample. Each sample was measured in its dry state and after adding the specified amount of fluid in the table above to achieve approximately 20% fill of the media volume. For each sample in each condition, threshold magnetic field strength was measured as a function of reader frequency (and as a function of distance to ensure the threshold behavior was consistent with separation distance), and working range was measured for a fixed reader frequency of 13.56 MHz and 20 dBm reader transmit power (100 milliwatts).

Fluid was added across the open surface of the fluid collection media of each sample using a syringe, and then distributed throughout the fluid collection media by compressing and releasing it several times between two glass slides. The amount of fluid added in each sample was verified by mass measurement before the tag performance measurements, and re-verified after completing the measurements on each sample. Mass data are shown in the following Table 4 alongside the measured working range in the dry and wet state.

Figure 9A:
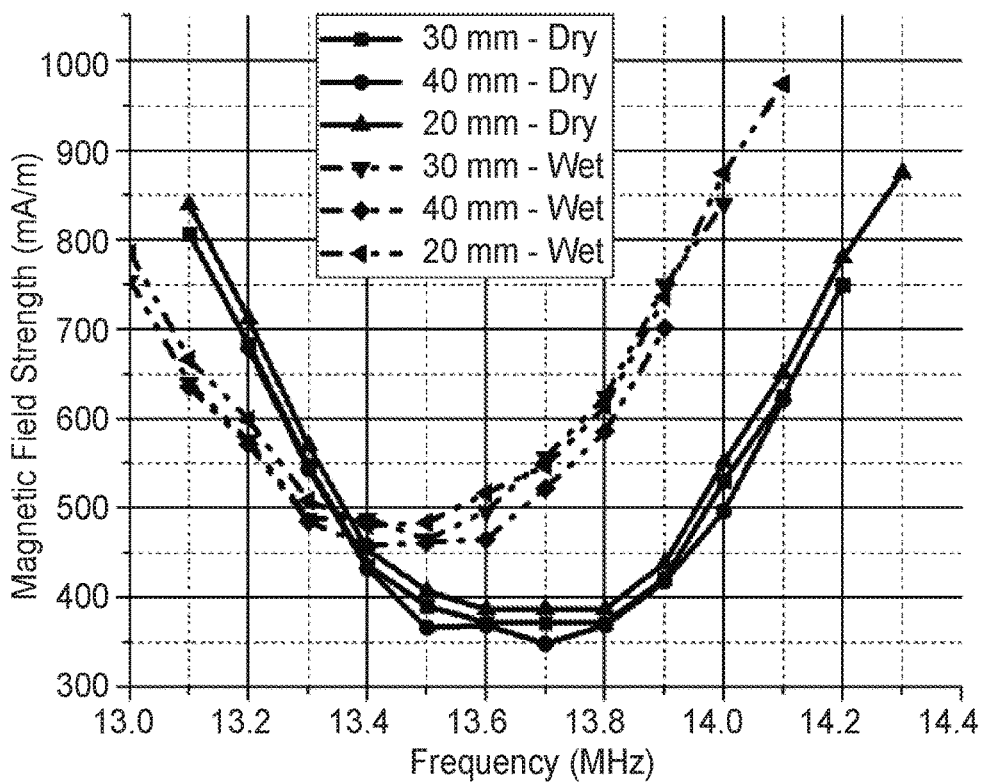
FIG. 9A plots of magnetic field strength versus frequency for Comparative Example B.
Figure 9B:
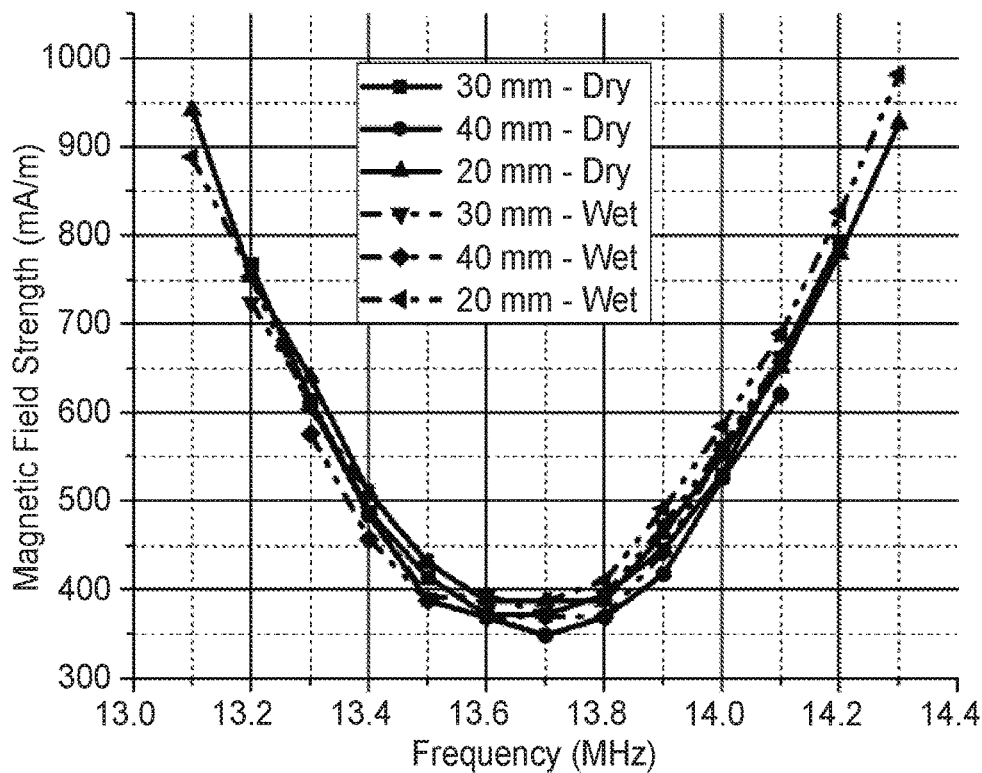
FIG. 9B illustrates plots of magnetic field strength versus frequency for Example F.

To provide further information about why this performance difference occurs, we can look at the threshold magnetic field strength measurements. Two representative samples' threshold magnetic field strength data are shown in FIGS. 9A-B. For Example B (and similarly for Example C), the presence of conductive fluid increases the magnetic field strength required to turn on its NFC tag, and shifts the resonance frequency (location of the minimum of the curve). Whereas for Example F (and Examples A, D, and E), there is minimal difference in threshold magnetic field strength between dry to wet. Because magnetic field strength generally decreases as a function of distance from the reader, these results mean Examples B and C will have reduced working range in the presence of conductive fluid, as was also seen in the direct measurements of working range above.

Reference throughout this specification to "one embodiment," "certain embodiments," "one or more embodiments," or "an embodiment," whether or not including the term "exemplary" preceding the term "embodiment," means that a particular feature, structure, material, or characteristic described in connection with the embodiment is included in at least one embodiment of the certain exemplary embodiments of the present disclosure. Thus, the appearances of the phrases such as "in one or more embodiments," "in certain embodiments," "in one embodiment," or "in an embodiment" in various places throughout this specification are not necessarily referring to the same embodiment of the certain exemplary embodiments of the present disclosure. Furthermore, the particular features, structures, materials, or characteristics may be combined in any suitable manner in one or more embodiments.

While the specification has described in detail certain exemplary embodiments, it will be appreciated that those skilled in the art, upon attaining an understanding of the

TABLE 4

| Sample ID | Sample Set | Dry mass (g) | Saline: mass of fluid added (g) | Saline: % of foam volume | Saline: mass of fluid at end of tests (g) | Saline: fluid loss during test | Working range - dry (mm) | Working range - wet (mm) | Loss of working range |
|---|---|---|---|---|---|---|---|---|---|
| A | Set 2 | 0.430 | 0.495 | 20% | 0.475 | −4% | 48 | 47 | −2% |
| B | Set 1 | 0.350 | 0.510 | 20% | 0.490 | −4% | 51 | 38 | −25% |
| C | Set 1 | 0.370 | 0.480 | 19% | 0.460 | −4% | 48 | 35 | −27% |
| D | Set 3 | 0.300 | 0.155 | 22% | 0.145 | −6% | 45 | 44 | −2% |
| E | Set 3 | 0.290 | 0.150 | 21% | 0.145 | −3% | 52 | 50 | −4% |
| F | Set 2 | 0.430 | 0.505 | 20% | 0.480 | −5% | 50 | 49 | −2% |

(Ambient conditions during these measurements were 72° F., 48% RH.)

Table 4 demonstrates that the two embodiments of the disclosure (Set 2 and Set 3) clearly improve the stability of the working range in the presence of conductive fluid. Those constructions also achieve the performance improvement while allowing the central portion of the circuit to remain in close contact with the fluid collection media.

foregoing, may readily conceive of alterations to, variations of, and equivalents to these embodiments. Accordingly, it should be understood that this disclosure is not to be unduly limited to the illustrative embodiments set forth hereinabove. In particular, as used herein, the recitation of numerical ranges by endpoints is intended to include all numbers subsumed within that range (e.g., 1 to 5 includes 1, 1.5, 2, 2.75, 3, 3.80, 4, and 5). In addition, all numbers used herein are assumed to be modified by the term "about." Furthermore, various exemplary embodiments have been described. These and other embodiments are within the scope of the following claims.

What is claimed is:

1. A radio-frequency (RF) sensor device comprising:
a substrate;
an antenna having at least a portion disposed on a first portion of the substrate;
a sensor disposed on a second portion of the substrate, the sensor being at least partially surrounded by the antenna, the sensor including an RF component electrically coupled to the antenna; and
a spacer layer attached to the first portion of the substrate adjacent to the antenna,
wherein the spacer layer has a thickness T, a relative permittivity k, and a figure of merit defined as the ratio of T (in micrometers) by k, the spacer layer has the figure of merit no less than 20 (micrometers).

2. The RF sensor device of claim 1, wherein the spacer layer has the figure of merit no less than 50.

3. The RF sensor device of claim 1, wherein the relative permittivity of the spacer layer is in the range from about 1.01 to about 4, and the thickness of the spacer layer is in the range from about 250 micrometers to about 1.0 mm.

4. The RF sensor device of claim 1, wherein the spacer layer comprises one or more low-dielectric constant materials including one or more of polymers, non-woven materials, woven materials, aerogels, or glasses.

5. The RF sensor device of claim 1, wherein the spacer layer is water-vapor resistant and configured to prevent moisture to penetrate therethrough to reach the antenna.

6. The RF sensor device of claim 1, wherein the spacer layer has a frame shape with a width corresponding to the width of the first portion of the substrate, the frame shape defining a window to accommodate a portion of the substrate on which the sensor is disposed.

7. The RF sensor device of claim 1, wherein the spacer layer includes a ribbed structure.

8. The RF sensor device of claim 1, wherein the spacer layer includes a closed-cell foam.

9. The RF sensor device of claim 1, wherein the spacer layer is disposed on the antenna to cover at least a portion of the antenna.

10. The RF sensor device of claim 1, wherein the spacer layer is disposed on the side of the substrate opposite to the antenna.

11. The RF sensor device of claim 1, further comprising a layer of insulating media to cover the sensor disposed on the substrate.

12. The RF sensor device of claim 1, further comprising a cover film to wrap components disposed on the substrate.

13. The RF sensor device of claim 12, wherein the cover film has a peripheral portion with an adhesive surface.

14. A radio-frequency (RF) sensor to measure a hydration level, comprising:
a substrate;
an antenna having at least a portion disposed on a peripheral portion of the substrate;
an absorption element comprising a fluid absorption material;
a spacer layer attached to the peripheral portion of the substrate adjacent to the antenna, the spacer layer has a thickness T, a relative permittivity k, and a figure of merit defined as the ratio of T (in micrometers) by k, the spacer layer has the figure of merit no less than 20; and
a sensor element disposed on the substrate, the sensor element being disposed on the absorption element and configured to measure the hydration level of the fluid collection media, the sensor element being at least partially surrounded by the antenna and electrically coupled to the antenna.

15. The RF sensor of claim 14, wherein the spacer layer has a frame shape with a width corresponding to the width of the peripheral portion of the substrate, the frame shape defining a window within which the sensor element is disposed and in contact with the fluid collection media.

16. The RF sensor of claim 14, wherein the spacer layer is sandwiched between the substrate and the absorption element.

17. The RF sensor of claim 14, wherein the spacer layer is disposed around a periphery of the absorption element.

18. The RF sensor of claim 14, wherein the spacer layer is disposed on the antenna to cover a least a portion of the antenna.

19. The RF sensor of claim 14, wherein the spacer layer is disposed on the substrate at the side opposite to the antenna.

20. The RF sensor of claim 18, further comprising a barrier layer to separate the substrate from the absorption element.

* * * * *

UNITED STATES PATENT AND TRADEMARK OFFICE
CERTIFICATE OF CORRECTION

PATENT NO. : 11,119,053 B2
APPLICATION NO. : 16/623883
DATED : September 14, 2021
INVENTOR(S) : Hameed et al.

Page 1 of 1

It is certified that error appears in the above-identified patent and that said Letters Patent is hereby corrected as shown below:

In the Claims

<u>Column 20</u>
Line 21, In Claim 14, delete "20" and insert -- 20 (micrometers) --, therefor.
Line 39, In Claim 18, delete "a least" and insert -- at least --, therefor.

Signed and Sealed this
Seventh Day of June, 2022

Katherine Kelly Vidal
*Director of the United States Patent and Trademark Office*